US012691445B2

(12) United States Patent
Markovsky et al.

(10) Patent No.: US 12,691,445 B2
(45) Date of Patent: Jul. 28, 2026

(54) IN-LINE TESTING DEVELOPMENT DIAGNOSTIC ANALYSIS

(71) Applicant: Charm Sciences, Inc., Lawrence, MA (US)

(72) Inventors: Robert J. Markovsky, Brentwood, NH (US); Robert Salter, Reading, MA (US); David W. Douglas, Andover, MA (US); Paul E. Graham, Dracut, MA (US); Alan C. Tran, Everett, MA (US); Ryan N. Sullivan, Lowell, MA (US)

(73) Assignee: Charm Sciences, Inc., Lawrence, MA (US)

( * ) Notice: Subject to any disclaimer, the term of this patent is extended or adjusted under 35 U.S.C. 154(b) by 344 days.

(21) Appl. No.: 16/975,460

(22) PCT Filed: Mar. 4, 2019

(86) PCT No.: PCT/US2019/020535
§ 371 (c)(1),
(2) Date: Aug. 25, 2020

(87) PCT Pub. No.: WO2019/169383
PCT Pub. Date: Sep. 6, 2019

(65) Prior Publication Data
US 2021/0016271 A1      Jan. 21, 2021

Related U.S. Application Data

(60) Provisional application No. 62/637,629, filed on Mar. 2, 2018.

(51) Int. Cl.
B01L 3/00       (2006.01)
G01N 1/14       (2006.01)
(Continued)

(52) U.S. Cl.
CPC .............. B01L 3/5023 (2013.01); G01N 1/14 (2013.01); G01N 21/8483 (2013.01);
(Continued)

(58) Field of Classification Search
None
See application file for complete search history.

(56) References Cited

U.S. PATENT DOCUMENTS 4,238,521 A * 12/1980 Charm .................. A23C 7/043
426/580
4,934,817 A * 6/1990 Gassenhuber ......... G01N 33/92
422/68.1
(Continued)

*Primary Examiner* — Lore R Jarrett
(74) *Attorney, Agent, or Firm* — MacCord Mason PLLC

(57) ABSTRACT

In-line testing and product delivery assemblies, methods, operations, and systems are shown and described. In one embodiment, an in-line testing and product delivery system includes a supply of product having at least one outlet with a valve closure and a downstream delivery line, a recirculation closed loop in fluid communication with the outlet and supply, and a reader to generate a rapid test result from a single use assay for detection of a presence or an absence of an analyte in the supply. The result provides monitoring of a detection of the analyte to block release of product supply into the delivery line.

16 Claims, 25 Drawing Sheets

(51) Int. Cl.
     *G01N 21/84*       (2006.01)
     *G01N 33/487*     (2006.01)

(52) U.S. Cl.
     CPC ................. *B01L 2300/0663* (2013.01); *B01L 2300/0825* (2013.01); *B01L 2300/1805* (2013.01); *G01N 33/487* (2013.01)

(56)               References Cited

U.S. PATENT DOCUMENTS

| | | | |
|---|---|---|---|
| 8,045,169 B2 * | 10/2011 | Hebert | G01N 21/253 |
| | | | 356/448 |
| 2011/0053291 A1 * | 3/2011 | Matsuda | G01N 33/54388 |
| | | | 436/514 |
| 2012/0012059 A1 * | 1/2012 | Arvidsson | A01J 5/045 |
| | | | 119/14.08 |
| 2012/0071342 A1 * | 3/2012 | Lochhead | B01L 3/502715 |
| | | | 435/5 |
| 2015/0251177 A1 * | 9/2015 | Kim | B01L 9/06 |
| | | | 435/287.2 |
| 2015/0276613 A1 * | 10/2015 | Markovsky | G01N 30/95 |
| | | | 436/164 |
| 2022/0291133 A1 * | 9/2022 | Graham | G01N 21/8483 |

* cited by examiner

IN-LINE TESTING DEVELOPMENT DIAGNOSTIC ANALYSIS

This application claims the benefit of PCT application Ser. No. 19/020,535, filed Mar. 4, 2019, which claims priority to U.S. provisional application No. 62/637,629, filed Mar. 2, 2018, all of which are incorporated herein by reference in their entireties.

FIELD OF THE TECHNOLOGY

The present disclosure relates generally to analytical testing, and more particularly to improved detection of an analyte of an in-line delivery system.

BACKGROUND

Reagent strips and films are often a helpful analytical tool in the fields of clinical chemistry, analytical medicine and food sanitation diagnostics. For example, it is advantageous to determine or to test, through quantitative or qualitative methods, various matrices, including body fluids such as serum and urine, and food, such as meat products, fruit, vegetables, milk, honey and the like. Such matrices can be tested for a variety of analytes including a variety of chemicals, biochemicals and biological molecules such as bacteria, antibiotics, for example, sulfa drugs, tetracyclines, beta-lactam drugs; toxins, such as aflatoxin, zearalonone, ochratoxin, T-2, and vomitoxin, pesticides such as organo-phosphates and carbamates, and active metabolites, either in materials or on the surface of materials or a combination thereof.

Generally, lateral flow assays are membrane-based test devices in which a sample that is suspected of containing the analyte of interest is placed at or near one end of the membrane strip. The sample is carried to the opposite end of the membrane strip by a mobile phase that traverses the membrane strip, for example by capillary action. While traversing the membrane strip, the analyte in the test sample, if any, encounters one or more reagents. The reagents can include binders for the analyte. Binders can be mobile and, therefore, flow with the sample, or be immobilized on the test strip as a capture agent. Depending on the test configuration, either the analyte binder, the analyte itself, or some other reagent in the test system will be captured by the immobilized capture agent and, thereby, produce a detectable signal. The signal can be generated by a label provided within the assay. The detectable signal can be measured, such as by an optical reader.

The presence and, in some cases, the concentration, of an analyte on a reagent strip may be determined by measuring the optical reflectance from an area of development on the strip. For example, the area of development on the strip may be an area of color development. Percent reflectance can be used to determine the result.

Testing commonly occurs in a controlled environment, such as a laboratory, but testing in non-laboratory settings is also common. In some applications speed and ease of use is particularly important. For example, in food processing it would be advantageous for tests to be run in non-laboratory settings because processors must wait for results. Further, it would also be advantageous for tests to be run on trucks during transport of the items. For that reason, it would be advantageous to accelerate the speed of testing, reduce the cost of equipment and tests, improve the ruggedness of the apparatus, and enhance the ease of use and simplicity of operation. In addition, it is advantageous to have confidence that test results are valid. Therefore, systems, methods and devices herein also assist in preventing fraudulent use of pre-run, known negative assays in place of true samples or use of assays pre-marked to provide a negative result that does not reflect the true nature of the sample. It is also desirable to increase the ruggedness of the assays, systems and test procedures.

Therefore, Applicants desire systems and methods for analyte detection and product delivery without the drawbacks presented by traditional systems and methods.

SUMMARY

This disclosure provides improved analyte detection and product delivery that is convenient, efficient, and safe for the user, particularly when used to detect a presence or absence of an analyte.

In one embodiment, an in-line testing and product delivery assembly includes a supply of product having at least one outlet; a sample feed in fluid communication with the supply of product; a reader; and a delivery line in fluid communication with the supply outlet and having a delivery output valve. Typically the reader receives a sample from the sample feed and generate a test result from an assay for detecting a presence or absence of an analyte. The reader may have an optical detector to image at least a first transmission of light on the assay and an incubator to incubate the assay. Typically, a detection of the analyte triggers a closure of the delivery output valve, whereas a detection of an absence of the analyte triggers an opening of the delivery output valve to release supply through the delivery line.

In one example, the reader includes a hood to removably receive a single-use rapid assay, and wherein the hood comprises a puncture tip protruding to puncture the assay. Further, the hood may include a sample supply line in fluid communication with the sample teed to dispense sample into the assay. For instance, the sample feed may be aligned adjacent the puncture tip to dispense sample into the assay at the puncture to increase rapid testing.

In certain examples, the reader includes an inclined cavity having an elongated channel to receive and maintain the assay in an inclined testing position. The inclined cavity may include a proximate portion and an opposing distal portion, wherein the distal portion positioned above the proximate portion at about a forty-five degree, or similar, incline.

In particular examples, the reader generates a definitive test result within about fifteen seconds to about one minute, for instance the reader generates a definitive test result within about thirty seconds. In addition, the assembly may include an auto-sampler that is generally in fluid communication with the sample feed. The sample feed may be a closed loop recirculation system about the supply of product. The assembly may include an auto-sampler in fluid communication with the closed loop system at a sample release valve, wherein the recirculation loop being in fluid communication with the outlet and having a re-entry fluid communication with the supply of product. At least a portion of the recirculation loop may be a single use disposable conduit and/or a cleanable conduit.

In certain examples, the reader's optical detector detects a first transmission of light on the assay and detects at least a subsequent transmission of light on the assay, and wherein incubation of the assay and detection of the transmissions of light on the assay generates the test result. Further, the reader may generate at least one borderline test result.

In another embodiment, an in-line testing and product delivery system includes a supply of product having at least one outlet, wherein the outlet includes at least one valve closure and a delivery line downstream of the valve closure; a recirculation closed loop in fluid communication with the outlet and the supply; a reader adapted to generate a rapid test result from a single use assay for detection of a presence or an absence of an analyte, and a sampler in fluid communication with the recirculation closed loop to provide a sample to the reader. Typically the reader has an inclined cavity to receive and maintain the assay in an inclined testing position and a puncture tip to puncture the assay. Typically, a detection of the analyte triggers a closure of the valve closure upstream of the delivery line, and a detection of an absence of the analyte enables release of the supply to the delivery line.

In certain rapid test result examples, the single use assay includes about a three millimeter overlap of a binder application area over a nitrocellulose membrane. Further, the single use assay may include about a thirty-one millimeter length absorbent pad.

In another embodiment, in an in-line testing and product delivery having a supply tank, a sample feed, and a downstream delivery, a reader controls access of a product between the supply tank and the downstream delivery and includes an inclined cavity to receive a single use assay; a sample portal in fluid communication with the sample feed and into alignment with the assay aligned in the cavity; a puncture tip extending in the cavity to puncture the assay; an optical detector adapted to monitor the assay; and an incubator to incubate the assay.

In a further embodiment, an in-line testing and product delivery assembly includes a supply of product having at least one outlet; a recirculation loop in fluid communication with the outlet and having a re-entry fluid communication with the supply of product; an autosampler to receive a sample from the supply of product; a reader receiving the sample from the autosampler and adapted to generate a test result from an assay for detecting a presence or absence of an analyte; and a delivery line in fluid communication with the supply of product and having at least one valve closure, and wherein a positive test result generated by the reader enables the valve closure, and a negative test result generated by the reader releases the product to a downstream delivery.

In particular examples, the supply of product includes a milk tank. The analyte may be toxins, antibiotics, chemicals, biochemical, pesticides, active metabolites, and a combination thereof. For instance, the analyte may be mycotoxin, aflatoxin, zearalenone, ochratoxin, T-2, vomitoxin, and a combination thereof. The reader may generate a definitive test result within about fifteen seconds to about one minute, for instance within about thirty seconds. In particular examples, the reader generates a definitive mycotoxin test result within about thirty seconds.

In some examples, the auto-sampler is aligned in fluid communication with the recirculation loop. The auto-sampler may be a drip sampler. The delivery supply line may be aligned in fluid communication with the recirculation loop. The recirculation loop may include a closure valve. The recirculation loop being a disposable conduit, a cleanable conduit, or the like. The recirculation loop may include a pump. The assembly may include a plurality of supplemental conduits.

In certain examples, the reader includes an incubator. The reader may perform a diagnostic test on the assay concurrently as the incubator incubates the assay. The reader may generate at least one borderline test result. The reader may perform one or more subsequent continuous readings to generate the test result after performing the first reading of the diagnostic test. The reader may perform one or more subsequent continuous readings and extends incubating of the assay to generate a definitive test result after performing the first reading of the diagnostic test.

In another embodiment of the disclosure, a method of in-line testing and product delivery includes circulating a product from a supply about a recirculation loop; receiving a sample of the product and generating a test result from an assay for detecting a presence or an absence of an analyte; releasing the product when generating a negative test result; and blocking a downstream delivery of the product when generating a positive test result.

In particular examples, receiving the sample includes autosampling the product. The method may include autosampling from the recirculation loop. The method may include blocking the downstream delivery of product includes enabling a delivery valve closure. Releasing the product may include enabling a recirculation valve closure. Generating the test result may include incubating the assay. Generating the test result may include reading a diagnostic test on the assay concurrently as an incubator incubates the assay. Generating the test result may include generating at least one borderline test result. Generating the test result may include performing one or more subsequent continuous reading of the diagnostic test. Generating the test result may include extending incubating of the assay after performing the first reading of the diagnostic test. Generating the test result may include extending incubating of the assay to generate a definitive test result after performing the first reading of the diagnostic test.

In certain examples, reading the diagnostic test includes performing about a thirty second diagnostic reading. Further, generating the test result may include reading a predetermined difference between a reflectance value on a control line and a reflectance value a test line. Generating a definitive test result may include reading a predetermined difference between a reflectance value of a control line and a reflectance value of test line, and a predetermined reflectance value on the control line.

In particular examples, the method may include monitoring a pre-test analysis on the assay and/or decoding a reference coding on the assay. For instance, to activate a corresponding channel in a multichannel reader and activate an incubation of the assay. Further, the method may include monitoring a pre-flow development along the assay. The method may include signaling an optical detector to perform continuing image detection of the assay to generate a test result, wherein the test result is a borderline test result. In addition, the method may include developing a subsequent image detection of the borderline test result to generate a definitive presence or absence test result.

In yet another embodiment, a method of analyzing a borderline test of an assay includes several image detections of the assay to provide a definitive presence or absence test result. In one example, the method includes incubating the assay in an incubation environment, aligning an optical detector in an optical path with the assay, signaling the optical detector to perform a first image detection, and signaling the optical detector to perform a second image detection. Typically, signaling the optical detector to perform a first image detection of the assay generates a borderline test result. Further, the method typically includes signaling the optical detector to perform at least a second subsequent image detection of the assay to generate a definitive presence or absence test result. Other examples include a variety of subsequent image detections as shown and described herein.

In yet other embodiments, a method of detecting an analyte from an assay includes aligning an optical detector in an optical path with the assay; signaling the optical detector to perform continuing image detection of the assay to generate a definitive presence or absence test result; and developing further image detection of the diagnostic test for a borderline test result. In some examples, the method may include incubating the assay in an incubation environment concurrently as the optical detector performs continuing image detection of the assay. In some exemplary embodiments, the method includes signaling the optical detector to perform a one minute image detection. Typically, detecting a definitive presence test result includes deactivating the system. Similarly, detecting a definitive negative test result includes deactivating the system.

In another embodiment a method of generating a definitive test result from an assay for detecting the presence or absence of an analyte includes incubating the assay in an incubation environment; reading a diagnostic test on the assay concurrently as an incubator incubates the assay; and performing continuous reading of the diagnostic test and incubating of the assay of a borderline test result to generate the definitive test result. In certain examples, reading the diagnostic test includes performing a one minute diagnostic reading. Typically, detecting the definitive positive test includes deactivating the system. Similarly, detecting a definitive negative test includes deactivating the system. Generating a definitive test result may include reading a predetermined difference between a reflectance value on a control line and a reflectance value a test line. Similarly, generating a definitive test result may include reading a predetermined difference between a reflectance value of a control line and a reflectance value of test line, and a predetermined reflectance value on the control line.

In other examples, the method includes monitoring a pre-test analysis on the assay. Further, the method may include decoding a reference coding on the assay. In addition, the method may include activating a corresponding channel in a multichannel reader and/or activating an incubation of the assay. The method may also include monitoring a pre-flow development along the assay.

In another aspect of the disclosure, an assay measurement apparatus to generate a diagnostic test result from an assay includes an optical detector and a microprocessor. The optical detector may be aligned in an optical path with the assay. The optical detector may be adapted to acquire an image detection on the assay due to an aberration on the assay. The microprocessor may be in communication with the optical detector. The microprocessor may be adapted to signal the optical detector to perform continuous image detection of the assay to generate the diagnostic test result.

The optical detector may comprise a decoding sensor that is adapted to align with the assay and decode a reference coding on the assay. The reference coding may activate a corresponding diagnostic test in the optical detector. The apparatus may include a multichannel reader and the reference coding may activate a corresponding channel in the multichannel reader. The apparatus may include an incubator and the reference coding may activate a corresponding incubation temperature.

The decoding sensor may be a color sensor. The color sensor may be a photodiode with sensitivity to wavelengths chosen from red, blue, green and a combination thereof. The decoding sensor may be an RFID reader. The decoding sensor may be a bar code reader.

In one example, the apparatus includes a light source. The light source may be an array of discrete light sources. For instance, the discrete light sources may comprise one light emitting diode and/or multiple light emitting diodes. The light emitting diodes may be colored diodes chosen from red, green, blue and a combination thereof. The light source may comprise an illumination profile suitable for reflecting on a test strip assay. The light source may be aligned with a light aperture, exposing light from the light source on the assay. A first mirror may be below the light aperture. A focusing lens may receive light from the first mirror. A second mirror may be positioned to direct light from the focusing lens to the optical detector. A lighting processor may be adapted to trigger the light source to emit light for a desired pattern. The lighting processor may include data storage for the desired light-emission pattern.

In another example, the optical detector will not generate a test result until the decoding sensor decodes the reference coding. The optical detector may be a light-to-voltage sensor. The optical detector may comprise a photodiode in the optical path with the assay coupled to an integrated circuit. The integrated circuit may be a monolithic integrated circuit. The optical detector may include an amplifier. The amplifier may be a translucence amplifier.

The apparatus may include a memory adapted to store information corresponding to an imaging parameter for the image detection. The decoding sensor may be chosen from a color sensor, a RFID reader, a bar code reader and a combination thereof. The optical detector may include an optical window that is adapted to block debris from contact with the optical detector. The optical detector may include an optics housing to enclose the optical detector and that is adapted to block debris from contact with the optical detector. The optical detector may monitor a diagnostic test progress. The optical detector may monitor a pre-test parameter prior to generating a diagnostic test result. The optical detector may monitor at least one pre-test parameter after the optical detector has acquired at least one image detection on the assay.

In another embodiment, in an assay measurement apparatus having an imaging detector and a microprocessor, a memory that is in communication with the microprocessor and is adapted to store information corresponding to an imaging parameter. The memory may include an instruction for monitoring a pre-test analysis on the assay. The memory may include an instruction for generating a diagnostic test result on the assay. The pre-test parameter may include a theoretical reflectance value.

In one example, the assay may include at least one test line and at least one control line, and whereby the theoretical reflectance value is a comparison between a reflectance value at the test line and a reflectance value at the control line. A reflectance value on the assay that is inconsistent with the theoretical reflectance value may indicate an inadequate flow on the assay. The inadequate flow may trigger a detectable signal to generate a no-result response. The reflectance value on the assay that is inconsistent with the theoretical reflectance value may indicate a prior analyte development on the assay. The reflectance values may suggest prior analyte development may trigger a detectable signal to deactivate the assay measurement apparatus. The reflectance value on the assay that is inconsistent with the theoretical reflectance value may indicate a contaminated optical path.

The contaminated optical path may trigger a detectable signal to generate a no-result response. The instruction for generating a test result may correspond to an image detection on the assay. The image detection may be an optical reflectance value or a transmission value. The assay may include at least one test line and at least one control line, and whereby the optical reflectance value is a comparison between a reflectance value at the test line and a reflectance value at the control line. The apparatus may be adapted to perform a continuous image detection of the assay. The assay may be a lateral flow assay. The assay may also be a lateral, capillary-flow, elongated test strip.

The test result may be determined within about thirty seconds of optical detector activation. The test result may be determined within about sixty seconds of optical detector activation. The apparatus may include a power source. The power source may be a vehicle battery. Further, the optical detector may be in communication with an onboard vehicle system.

In other embodiments, an assay measurement apparatus to generate a test result from an assay may include an imaging detector and a microprocessor with an associated memory in communication with the microprocessor. The imaging detector may be adapted to decode a reference coding on the assay and to acquire an image detection on the assay due to an aberration on the assay. The microprocessor may be adapted to signal the imaging detector to generate the test result. The memory may be in communication with the microprocessor and may be adapted to store information corresponding to a plurality of imaging parameters. The memory may include a parameter for monitoring a pre-test analysis on the assay. The memory may include a parameter for generating the diagnostic test result from the assay.

A reference coding may activate a corresponding diagnostic test in the optical detector. A multichannel reader and the reference coding may activate a corresponding channel in the multichannel reader. The apparatus may include an incubator and the reference coding may activate a corresponding incubation temperature.

The imaging detector may be adapted to decode the test reference coding and comprise a decoding sensor. The decoding sensor may be a color sensor. The color sensor may be a photodiode with sensitivity to wavelengths chosen from red, blue, green and a combination thereof. The decoding sensor may be an REED reader. The decoding sensor may also be a bar code reader.

Typically, the apparatus includes a light source. The light source may be an array of discrete light sources. The discrete light sources may comprise light emitting diodes. The light emitting diodes may be colored diodes chosen from red, green, blue and a combination thereof. The light source may comprise an illumination profile suitable for reflecting on a test strip assay. The light source may be aligned with a light aperture exposing the light source on the assay. The light source may include a first mirror below the light aperture. A focusing lens may receive light from the first mirror. A second mirror may be positioned to direct light from the focusing lens to the optical detector. A lighting processor may be adapted to trigger the light source to emit light for a desired pattern. The lighting processor may include data storage for the desired light-emission pattern. The optical detector may not generate a test result, or even initiate reading of the test, until the decoding sensor decodes the reference coding.

The optical detector may be a light-to-voltage sensor. The optical detector may comprise a photodiode coupled to an integrated circuit in the optical path with the assay. The integrated circuit may be a monolithic integrated circuit. The optical detector may include an amplifier. The amplifier may be a translucence amplifier. The optical detector may include an optical window that is adapted to block debris from contact with the optical detector. The optical detector may also include an optics housing to enclose the optical detector and that is adapted to block debris from contact with the optical detector.

In some examples, the optical detector may monitor a diagnostic test progress. The optical detector may monitor a pre-test parameter prior to generating a diagnostic test result. Further, the optical detector may monitor at least one pre-test parameter after the optical detector has acquired at least one image detection on the assay. The pre-test parameter may include a theoretical reflectance value. The assay may include at least one test line and at least one control line, and whereby the theoretical reflectance value is a comparison between a reflectance value at the test line and a reflectance value at the control line. Theoretical reflectance values may also be a pre-set preset parameter value for the control tine or the test line. For instance, the control line may be the theoretical reflectance value. A reflectance value on the assay that is inconsistent with the theoretical reflectance value may indicate an inadequate flow on the assay. The inadequate flow may trigger a detectable signal to generate a no-result response. Further, a reflectance value on the assay that is inconsistent with the theoretical reflectance value may indicate a prior analyte development on the assay. The prior analyte development may trigger a detectable signal to generate a no-result response. Yet further, a reflectance value on the assay that is inconsistent with the theoretical reflectance value may indicate a contaminated optical path. The contaminated optical path may trigger a detectable signal to get a no-result response reading, and/or deactivate the assay measurement apparatus.

An instruction for generating a test result may correspond to an image detection on the assay. The image detection may be an optical reflectance value. The assay may include at least one test line and at least one control line, and whereby the optical reflectance value is a comparison between a reflectance value at the test line and a reflectance value at the control line. The apparatus may be adapted to perform a continuous image detection of the assay. The assay may be a lateral flow assay. For instance, the assay may be a lateral, capillary-flow, elongated test strip. Further, the apparatus may include a means for a power source.

In yet another embodiment, a lateral flow assay for the detection of an analyte and having a test zone and a control zone, a surface having a reflectance profile includes at least one flow reference and at least one test result reference. The at least one flow reference area may be adapted to enable monitoring of a pre-flow development along the assay. The at least one test result reference area may be adapted to enable monitoring a pre-test detection of the analyte on the assay.

The reflectance profile may include a theoretical light reflectance measurement. The theoretical light reflectance measurement may comprise a no-flow development theoretical value. The no-flow development value may be a reflectance value of about 85. A reflectance value of greater than about 85 may generate a signal to deactivate the detection of the analyte. The flow reference area may include at least one downstream flow reference line. The downstream flow reference line may include a theoretical reflectance value after the flow reference line receives reagent flow thereon. The flow reference area may include both an intermediary flow reference line and a downstream flow reference line. The intermediary flow reference line may include a theoretical reflectance value after the flow reference line receives reagent flow thereon. The theoretical light reflectance measurement may comprise a no-analyte pre-test development theoretical value. The flow reference may also be the control zone.

The test result reference area may include at least one test line having a theoretical reflectance value. The test result reference area may include at least one control line having a theoretical reflectance value. The test result reference area may include at least one test line having a theoretical reflectance value and at least one control line having a theoretical reflectance value. A pre-set difference between the at least one test line's theoretical reflectance value and the at least one control line's theoretical reflectance value may activate a test result. Further, a pre-set difference between the at least one test line's theoretical reflectance value and the at least one control line's theoretical reflectance value may trigger an error. The error may withhold a test result.

In other embodiments, a lateral, capillary-flow elongated test strip includes a test zone, a control zone and a surface having a reflectance profile. The lateral, capillary-flow elongated test strip may have at least one reagent for the detection of at least one analyte in a sample. The test zone may include immobilized thereon a test zone capture agent that is adapted for capturing the at least one reagent. The control zone may include at least one control zone capture agent having a different binding affinity for the at least one reagent. The reflectance profile may be adapted to enable monitoring of the test strip continuously until the detection of the analyte. Typically, the test strip generates a detectable signal for detecting the analyte in the sample. In some examples, inadequate control line development, for instance according to reflectance and/or transmission at the control line, may trigger an error. In these examples, the error may trigger a signal to generate a no-result response.

The test strip may comprise a coding system having at least one reference code with a corresponding testing sequence. The testing sequence may include at least one temperature adjustment parameter. Further, the testing sequence may include an optical reader test parameter. The optical reader test parameter may include a reader channel selection. The reader test parameter may include an associated feature chosen from a standard curve, a does-response curve and a combination thereof. The reader test parameter may include at least one associated positive control point and at least one associated negative control point. The coding system may include a color matrices. The color matrices may include a color chosen from red, blue, green and combination thereof. The color matrices may be associated with a corresponding diagnostic test. The coding system may include a bar code. The coding system may include an RFID tag.

The test strip may include a first end having a sample absorbing material. The test strip may include a peel strip to introduce sample onto the sample absorbing material. The peel strip may include a peel tab at one end of the peel strip to facilitate movement of the peel strip. The sample absorbing material may be adapted to receive about 0.1 to about 1.0 mL of a fluid. The sample absorbing material may comprise a dry cellulosic material. Further, the test strip may include an opposed second end having a reactor detector material. The test strip may include a releasing area having a mobile phase receptor for the at least one analyte. The test strip may be sized and adapted to be enclosed within a test strip cavity. Further, the test strip may be sized and adapted to be enclosed within a test strip cavity of a removable incubation module. Typically, the test strip is adapted for selecting the detection of a diagnostic test group chosen from an antibiotic analyte, toxic analyte, analyte class, a combination thereof and the like.

The test zone may include at least one analyte reference line having a theoretical reflectance value. The theoretical reflectance value may be associated with a flow parameter on the test strip. The test zone surface may include a first analyte reference line having a first theoretical reflectance value and a second analyte reference line having a second theoretical reflectance value. The control zone surface may include at least one control line having a theoretical reflectance value. For instance, the theoretical reflectance value may be an optical reflectance value. The control zone may include a first control line having a first theoretical reflectance value and a second control line having a second theoretical reflectance value. In some examples, the reflectance profile is adapted to enable monitoring of the test strip prior to the detection of the analyte. Further, the test result may be detected within about thirty to about sixty seconds.

In yet another embodiment, a lateral, capillary-flow elongated test strip includes a test zone including immobilized thereon a test zone capture agent adapted for capturing at least one binder, a control zone including at least one control zone capture agent having a different binding affinity for the at least one binder, a surface having a reflectance profile adapted to enable monitoring of the test strip and a coding system having at least one coding signal, for instance a coding to correspond to a testing sequence to characterize the test strip. The reflectance profile may include at least one flow reference area adapted to enable monitoring of a flow development along the assay, and at least one monitor reference area adapted to enable monitoring of detection of the analyte on the assay.

The testing sequence may include at least one temperature adjustment parameter. The testing sequence may include an optical reader test parameter. The optical reader test parameter may include a reader channel selection. The optical reader test parameter may include an associated feature chosen from a standard curve, a does-response curve and a combination thereof. Further, the optical reader test parameter may include at least one associated positive control point and at least one associated negative control point. The coding system may include a color matrix. The color matrices may be associated with a corresponding diagnostic test. The coding system may include a bar code. The coding system may include an RFD tag.

In some examples, the test strip may include a first end having a sample absorbing material. The test strip may include a peel strip to introduce sample onto the sample absorbing material. The peel strip may include a peel tab at one end of the peel strip to facilitate movement of the peel strip. The sample absorbing material may be adapted to receive about 0.1 to about 1.0 mL of a fluid. The sample absorbing material may comprise a dry cellulosic material. The test strip may include an opposed second end having a reactor detector material. The test strip may include a releasing area having a mobile phase receptor for the at least one analyte. The test strip may be sized and adapted to be enclosed within a test strip cavity. Further, the test strip may be sized and adapted to be enclosed within a test strip cavity of a removable incubation module. Typically, the test strip is adapted for selecting the detection of a diagnostic test group chosen from an antibiotic analyte, toxic analyte, analyte class, a combination thereof and the like, either quantitatively, qualitatively or both.

The test zone may include at least one analyte reference line having a theoretical reflectance value. Typically, the theoretical reflectance value is associated with a flow parameter on the test strip. The test zone may include a first analyte reference line having a first theoretical reflectance value and a second analyte reference line having a second theoretical reflectance value. The control zone may include at least one control line having a theoretical reflectance value. The theoretical reflectance value may be an optical reflectance value. A control zone may include a first control line having a first theoretical reflectance value and a second control line having a second theoretical reflectance value. The theoretical light reflectance measurement may comprise a no-flow development theoretical value. The no-flow development value may be a reflectance value of about 85. The reflectance value of greater than about 85 may generate a signal to deactivate the detection of the analyte.

In other examples, the flow reference area may include at least one downstream flow reference line. The downstream flow reference line may include a theoretical reflectance value after the flow reference line receives reagent flow thereon. The flow reference area may include an intermediary flow reference line and a downstream flow reference line. The intermediary flow reference line may include a theoretical reflectance value after the flow reference line receives reagent flow thereon. The theoretical light reflectance measurement may comprise a no-analyte pre-test development theoretical value. The test result reference area may include at least one test line having a theoretical reflectance value. The test result reference area may include at least one control line having a theoretical reflectance value. The test result reference area may include at least one test line having a theoretical reflectance value and at least one control line having a theoretical reflectance value. A pre-set difference between the at least one test line's theoretical reflectance value and the at least one control line's theoretical reflectance value may activate a test result. Further, a pre-set difference between the at least one test tine's theoretical reflectance value and the at least one control line's theoretical reflectance value may trigger an error. Typically, the error withholds a test result, including generating a no-result response.

In yet another embodiment, in an assay system having an incubator and a reader to generate a test result from an assay, a sensor may be adapted to continuously monitor the assay while the incubator incubates the assay and the reader generates the test result. The sensor may be adapted to deactivate the incubator when the sensor detects an aberration on the assay. The sensor may be an optical detector. The optical detector may be adapted to detect a reflectance value. The assay may include at least one test zone and at least one control zone, and whereby the reflectance value is a comparison between a reflectance value at the test zone and a reflectance value at the control zone. Further, if the reader and/or incubator hood is opened during incubation or reading, a signal may generate a no-result response. Additionally, if the assay is removed before a test result is generated, a signal may generate a no-result response.

In some examples, the incubator may be deactivated when the sensor detects a reflectance value on the assay that is inconsistent with a predetermined theoretical reflectance value on the assay. For instance, a reflectance value on the assay that is inconsistent with the theoretical reflectance value may indicate an inadequate flow on the assay. Further, a reflectance value on the assay that is inconsistent with the theoretical reflectance value may indicate a prior analyte development on the assay. Similarly, a reflectance value on the assay that is inconsistent with the theoretical reflectance value may indicate a contaminated optical path.

In other examples, the sensor may be adapted to deactivate the reader when the sensor detects an aberration on the assay. The sensor may be an optical detector. The optical detector may be adapted to detect a reflectance value. The assay may include at least one test zone and at least one control zone, and whereby the reflectance value is a comparison between a reflectance value at the test zone and a reflectance value at the control zone. A no-result response may be generated when the sensor detects a reflectance value on the assay that is inconsistent with a predetermined theoretical reflectance value on the assay. A reflectance value on the assay that is inconsistent with the theoretical reflectance value may indicate an inadequate flow on the assay. Further, reflectance value on the assay that is inconsistent with the theoretical reflectance value may indicate a prior analyte development on the assay likewise, a reflectance value on the assay that is inconsistent with the theoretical reflectance value may indicate a contaminated optical path.

The sensor may be a decoding sensor. The decoding sensor may be chosen from a color sensor, a RFID reader, a barcode reader and a combination thereof. Typically, the sensor is triggered with an activation element chosen from a hood sensor, an incubator sensor, a trigger switch and a combination thereof.

The apparatus may include a housing that is adapted to substantially enclose the reader and the incubator. The housing may include insulation adapted to withstand deformation during the incubation. The housing may also include a cavity adapted to secure the assay and receive light from the reader. The cavity may include an optical aperture to receive light from the reader. The cavity may include an adjustable fastener adapted to position the cavity in an optical path with the reader. The cavity may include insulation adapted to withstand deformation during an incubation period. The assay may be a lateral, capillary-flow test strip. And thereby the housing may include a removable optical window adapted to block debris from the sensor. The removable optical window may include a handle. The removable optical window may be cleanable. Similarly, the removable optical window may be disposable. Additionally, the removable optical window may be slide-mounted. The housing may include an air opening. The air opening may include a cap.

In particular examples, the system may include a user interface. The user interface may include an integrated circuit board, for example to support a display board. The user interface may also be adapted to view flow development. Similarly, the user interface may be adapted to view the test result, including a no-result response. The user interface may also be adapted to view flow development after the reader has detected at least one flow development on the assay.

In another embodiment, a lateral flow assay system to generate a test result from an assay includes an incubator that is adapted to incubate the assay and a reader that is adapted to read a diagnostic test on the assay. The assay may undergo a change when contacted with a sample to generate the test result.

In some examples, the system includes a removable assay module. The removable assay module may include an assay cavity adapted to align the assay with the reader. The assay may be a lateral flow test strip. Thereby, the assay cavity may be sized to receive the lateral flow test strip. The removable assay module may include a hood. The hood may enclose the assay in a closed testing position and expose the assay in an open access position.

Further, the removable assay module may include a bottom face adapted to align with at least one light aperture on the reader. The bottom face may include an adjustment fastener adapted to secure the assay cavity in an optical alignment with the reader. The bottom face may also include an engagement lip to position the bottom face with the reader. The removable assay module may include at least one optical window. The removable assay module may be adapted to be removed from the system and cleaned from debris.

In some examples, the incubator includes an insulated base. The incubator may be a temperature adjustable incubator. The temperature adjustable incubator may include at least one temperature control. Thereby, the temperature adjustable incubator may include localized temperature variations. For instance, the incubator may compensate for localized temperature variations. The incubator may compensate for localized temperature variations with an analog, proportional circuit. In other examples, the incubator may compensate for localized temperature variations with a digital control circuit, for instance by utilizing a PID algorithm or PID controller. Further, the temperature adjustable incubator may include an embedded temperature sensor. The temperature adjustable incubator may include a potentiometer. The incubator may include a heater. The heater may be chosen from a ceramic heater, a resister heater element and the like. Similarly, the incubator may include a cooling system. In yet other examples, the incubator incubates the assay in a means for creating an incubation environment.

The reader may perform continuous image detection of the assay to generate the test result. The continuous image detection may include monitoring a pre-flow development along the assay, including monitoring for excessive flow and inadequate flow along the assay. The reader may include a light source oriented in a predetermined pattern with respect to the assay. The light source may include a first mirror below the light source. The light source may include a focusing lens adapted to receive light from the first mirror. Further, the light source may include a second mirror positioned to direct light from the focusing lens to the reader.

In particular examples, the reader may include a sensor. The sensor may be an optical detector that is aligned with a light source for detecting transmission of light through the assay. For instance, transmission embodiments herein may include analysis of refracted light from the assay. The sensor may be a decoding sensor. The decoding sensor may be adapted to decode at least one reference code having a corresponding testing sequence on the assay. Further, the reader may include multiple channels. Each of the channels may include an associated feature chosen from a standard curve, a does-response curve, a positive cutoff value, a negative cutoff value and the like.

In yet further embodiments, a method of generating a test result from an assay includes incubating the assay in an incubation environment and reading a diagnostic test on the assay concurrently as the incubator incubates the assay. The method may include sensing the assay continuously while the incubator is incubating the assay. The method may include deactivating the incubator when sensing an aberration on the assay. The method may include removing a removable assay module, for example for cleaning debris, or the like, from the assay module. The method may include adding a test sample to a test medium to create the assay. The method may also include enclosing the test medium within the reader. The method may include positioning a sensor relative to the test medium so that a change on the test medium is detectable by the sensor. The method may include decoding a reference coding on the assay. Thereby, the method may include selecting a channel in the reader corresponding to the reference coding on the assay. Further, the method may include incubating the assay within the incubator according to the reference coding on the assay.

In one embodiment, a method for managing test data includes generating a test result from a testing instrument reader; linking an application on a partner device to the testing instrument, thereby enabling test result output communication between the testing instrument and the partner device; subscribing a first test result output from the instrument to the partner device; and transmitting at least one second result output associated with the first output and selected from the group consisting of an operator identification, a sample identification, a lot number, a geographical location, a geographical coordinate, a sample note, and a test result note.

In particular examples, the method includes establishing authorized connection between the instrument and the partner device. Further, the partner device application may scan for an enabled testing instrument. The method may include real time exporting of the result outputs from the testing instrument. In certain examples, the method includes relaying result outputs from the partner device to an external storage configuration.

In another embodiment, a method for relaying test data generated from a sample on a testing instrument includes performing a diagnostic test on the testing instrument; interfacing the testing instrument with a mobile partner device having a corresponding data communication interface to establish enabled data communication with the testing instrument; transforming the test result into a result output format suitable for transmission, and establishing data communication exchange of the result output between the testing instrument and the partner device; and relaying the result output from the partner device to an external storage configuration. In certain examples, the testing instrument may include one or more of the following: a housing, a receiving port to receive the sample on a sample apparatus, a reading device to generate a test result from the sample apparatus, and a data communication interface.

In particular examples, the method includes establishing data communication between the testing instrument and the partner device, for instance linking an application on the partner device to the testing instrument. The partner application may scan for an enabled testing instrument. The partner application may subscribe data from the testing instrument. The method may include real time exporting of the result output from the testing instrument for logging a plurality of subsequent sample result outputs. Further, the method may include merging the plurality of sample result outputs and associated geographical locations, and mapping the plurality of result outputs. And in particular examples, the method may include generating a map display indicative of a toxin mapping outbreak. The method may include establishing authorized wireless connection between the testing instrument and the partner device, for instance with a Bluetooth® Low Energy (BLE), dongle, or similar system. The method may include establishing a host IP address connection between the partner device to the external storage configuration.

In some examples, performing the diagnostic test includes receiving a test strip sample apparatus and imaging the test strip sample apparatus to generate the test result. In some examples, performing the diagnostic test includes receiving a plate sample apparatus and imaging the plate, for instance a peel plate, sample apparatus to generate the test result. In some examples, performing the diagnostic test includes receiving a swab sample apparatus and analyzing the swab sample apparatus to generate the test result. In some examples, performing the diagnostic test includes incubating the sample apparatus. In certain examples, the method includes transmitting at least one sample identifier corresponding to an individual sample test result selected from the group consisting of an operator identification, a sample identification, a lot number, a geographical location, a geographical coordinate, a sample note, and a test result note. In particular examples, relaying to the external storage includes transmitting to a remote host website. Further, in particular examples, relaying to the external storage includes transmitting to a remote host server. In certain examples, the partner device comprises a smart phone having a data processing program as a downloadable application program. The partner device may have an indicator, and when activated providing a pairing signal, and wherein the indicator providing a visual indicia of pairing to the testing instrument. The method may also include establishing a secondary messaging data communication exchange between the testing instrument and the partner device.

In yet another embodiment, a method for use with a testing instrument and a host site adapted to support test result data includes connecting to an enabled testing instrument having a first mode of operation to perform at least one test on a sample, and in a second mode the instrument having a data communication interface communicating a result output transmission; receiving authorized result output transmissions; and transforming a plurality of the result outputs into a data display.

In certain examples, the method includes storing the plurality of result output data in a first database. Establishing the result output communication may first include establishing data communication with a partner device. For instance, the partner device may be a mobile phone, a tablet, a general purpose computer, a PDA, a digital media player, a digital camera, a wireless information device, and the like. In some examples, the data may insure that properly tested food products are delivered most efficiently to an assigned destination depending on test results. In other examples, the data may be collected from a multiplicity of sites and sources and combined, for illustrative purposes only, into a single database using low cost tools and existing test instruments.

Still another embodiment of the present disclosure includes a central station external storage configuration, for instance a central station to be a Web Hosted external storage configuration. In particular examples, the external storage configuration is assigned a public, static IP address to which any of the available, deployed instruments transmit test data, when available.

Another embodiment of the disclosure includes an integrated system of data handling with minimal operator intervention. In some examples, setup at the instrument requires downloading and installing the app on the smart-phone, attaching the blue-tooth adapter to a power source, pairing the Bluetooth® device, or the like device, to the smart-phone and then launching the app. Real time display of the test data on the smart-phone may provide the user that the test data was properly transmitted to the phone and allows for notes to be appended to the test data as shown and described herein.

In certain examples, with GPS enabled in the smartphone, the test data may contain the latitude and longitude where the test was performed. In these methods, once the test data packet has been collected to the phone, the app handles communication with the host central station attempting transfers when adequate signal strength is available. Integrated communication protocol insures that the data remains buffered in the phone until a signal from the host indicates successful collection.

The above summary was intended to summarize certain embodiments of the present disclosure. Embodiments will be set forth in more detail in the figures and description of embodiments below. It will be apparent, however, that the description of embodiments is not intended to limit the present inventions, the scope of which should be properly determined by the appended claims.

BRIEF DESCRIPTION OF THE DRAWINGS

Embodiments of the disclosure will be better understood by a reading of the Description of Embodiments along with a review of the drawings, in which.

DESCRIPTION OF EMBODIMENTS

Figure 1:
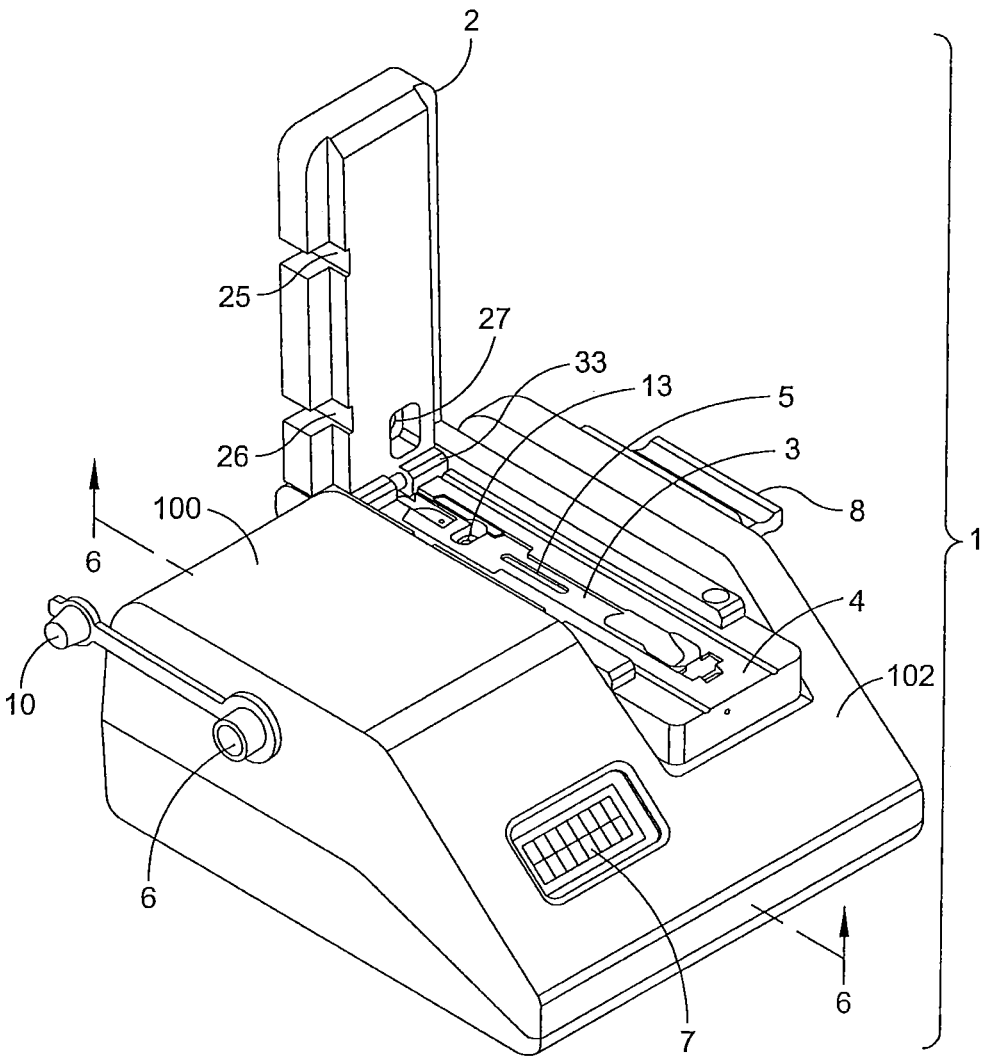
FIG. 1 is a front perspective view of one embodiment of a lateral flow assay system, with an open hood illustrating cavity and base components.

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms. It will be understood that the illustrations are for the purpose of describing embodiments of the disclosure and are not intended to limit the disclosure or any invention thereto.

In some embodiments, the testing instrument is a lateral flow assay system configured to receive an assay sample apparatus and analyze the assay to generate a diagnostic test result. Typically, the assay sample apparatus is a capillary-flow test strip. However, it is within the spirit of this disclosure for any of the assay apparatuses herein to be assays other than capillary-flow test strips.

As introduced in FIG. 1, a lateral flow assay system 1 is shown embodied according to the present disclosure. Lateral flow assay system 1 includes a combined reader 100 and incubator 102. Reader 100 typically includes an imaging detector, such as a sensor, while incubator 102 typically includes an insulated base 4. In some embodiments, the insulated base is a removable assay module 104. Typically, reader 100 first monitors an assay for one, or more, monitoring values, including flow rate, prior analyte development and debris. In various examples, if a proper monitoring value is detected by system 1, incubator 102 incubates the assay and reader 100 generates a test result. However, if an inconsistent monitoring value is detected, system 1 may generate a no-result response.

As shown in FIG. 1, lateral flow assay system 1 is configured to receive an assay and analyze the assay to generate a diagnostic test result. Typically, the assay is a capillary-flow test strip. However, it is within the sprit of this disclosure for any of the assays herein to be other lateral flow assays.

FIG. 1 shows a housing enclosing the reader 100 and incubator 102 as an integral diagnostic unit. Other embodiments include a housing that partially encloses components of lateral flow assay system 1. Typically, the reader includes cavity 3 to receive the assay, and a hood 2 to enclose the assay. The housing may have an exterior and interior, and may be opened, for instance hood 2, to receive an assay into cavity 3. As illustrated in FIG. 1, hood 2 may be lifted and the assay inserted into a heating cavity such as a metallic, for example aluminum, cavity within incubator 102. Typically, cavity 3 is surrounded by insulating material, such as a plastic material, for example a thermoplastic such as polyoxymethylene, known as Delrin (DELRIN is a registered trademark of DuPont) to insulate cavity 3, and does not deform when heated to the temperatures required for generating a test result.

Figure 19:
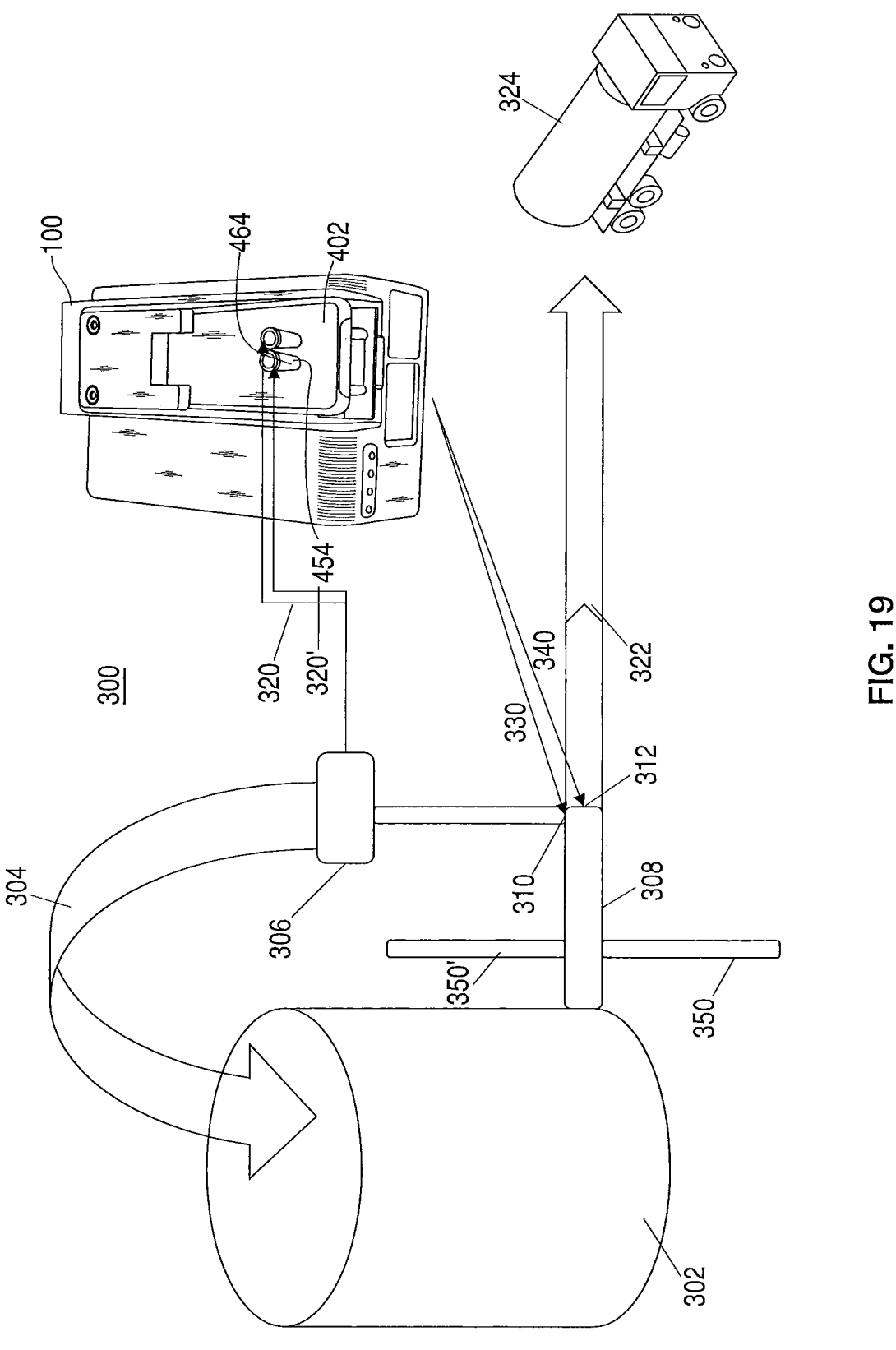
FIG. 19 is a schematic of one embodiment of an in-line testing assembly and method.
Figure 19A:
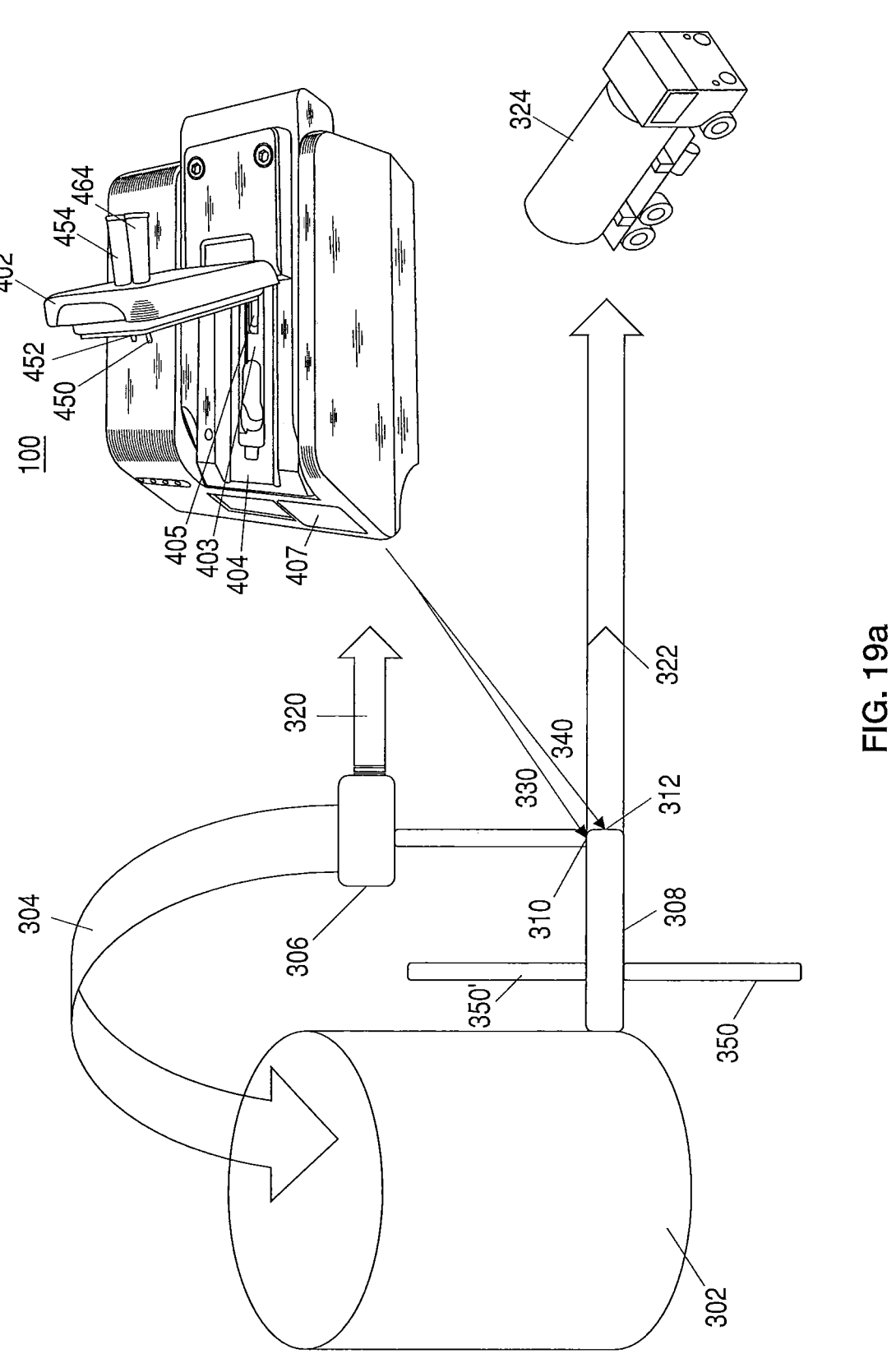
FIG. 19*a* is a schematic of another embodiment of an in-line testing assembly and method.
Figure 22:
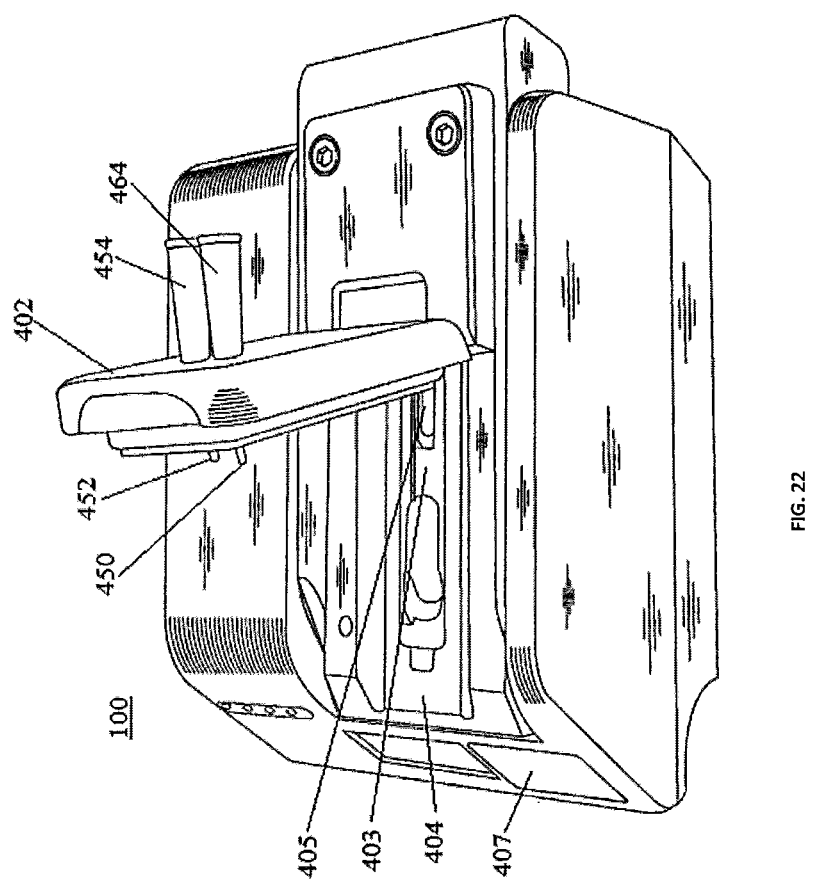
FIG. 22 is a side view of an isolated lateral flow assay system introduced in FIG. 19, with elements removed for clarity.
Figure 22A:
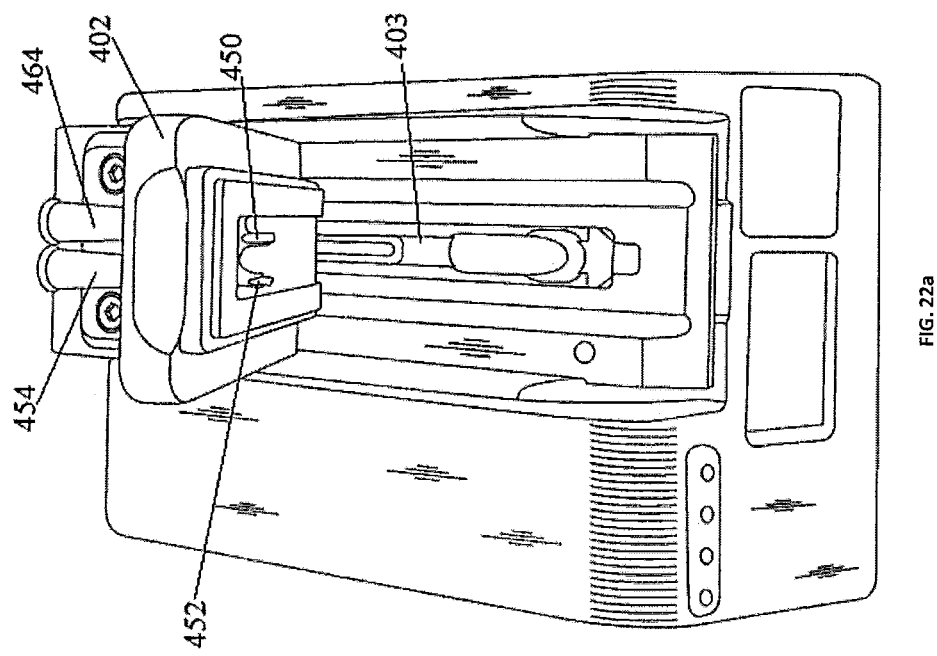
FIG. 22*a* is a front perceptive view of an isolated lateral flow assay system introduced in FIG. 19, with elements removed for clarity.

As shown in FIGS. 1, 19*a*, and 22*a*, hood 2, 402, 502 may be opened into an access position to receive and/or remove an assay within cavity 3, 403 of insulated base 4. Hood 2, 402, 502 may also be configured to substantially seal cavity 3 to enclose the assay in a closed testing position. Openings 25, 26 and 27, in hood 2, 402, 502 allow access to adjustment fasteners 11, 12 and 13 (see FIG. 8), including screws and the like, when hood 2, 402, 502 is in a closed position. In other examples, adjustment fasteners may also be accessed when hood 2, 402, 502 is positioned in an open access position. Typically, adjustment fasteners align cavity 3 in relation to optics, for instance an imaging detector described hereinafter, so that changes on the assay may be detected. For example, test strips may have multiple line developments in various areas on the test strip, as described hereinafter and introduced in FIG. 7. By allowing fine cavity adjustment with the adjustment fasteners through openings 25, 26 and 27, costly and cumbersome system recalibration may be minimized, or avoided. For instance, depending on a particular assay, flow, test and control lines may be in a variety of different position along the assay, as explained below, which may trigger an unexpected reflection, or transmission, value if cavity 3, 403 is not properly adjusted.

As introduced above, cavity 3, 403 may be configured to receive the assay, such as a lateral flow test strip, to position and maintain the assay in an optical alignment with reader 100. In some examples, cavity 3 is shaped with an elongated channel, for instance to receive a lateral, capillary-flow test strip.

Some embodiments of reader 100 are optical analysis readers, which often include a light source and an imaging detector, for example a sensor, that is aligned such that the light from the light source shines onto the assay and is then reflected onto the imaging sensor. An example of optical reader components useful in embodiments herein is described in U.S. Pat. No. 6,124,585 (Apparatus for measuring the reflectance of strips having non-uniform color), issued Sep. 26, 2000, and incorporated herein by reference. Typically, the presence and, in some cases, the concentration, of an analyte on an assay may be determined by measuring, for instance, the optical reflectance from an area of development on the assay. In some examples, percent reflectance may be used to determine the result. In other examples, transmission may be used to detect the result. For instance, the assay may be transparent and include a surface having a transmission profile, similar to the reflectance profile discussed below. This structure and function described in that patent may be adapted by those of ordinary skill in the art in accordance with the disclosure herein to obtain a functioning unit.

Reader 100 may comprise a variety of light sources, including an incandescent bulb, a fluorescent tube, a light emitting diode or the like. In some examples, the light source may be an array of discrete light sources, for instance colored light emitting diodes chosen from red, green, blue and a combination thereof. In yet other examples, the light source may be an individual light source, for instance a singular diode. Typically, the light source is configured and current driven to emit an illumination pattern suitable for reflecting onto the assay, for instance along an elongated test strip. As shown in FIG. 1, light can be directed to the assay, for example through aperture 5 in cavity 3, and then reflected off the assay, back through the cavity aperture 5 and directed to an optical detector.

In one example, an optics circuit board 31 (see FIG. 6) may have a plurality of light emitting diodes (LEDs) mounted thereon, for instance in a predetermined pattern around light-emitting aperture 5. The LEDs may be mounted on one side of optics circuit board 31. An optical detector array may be mounted to the reverse side of the same optics circuit board 31. Further, a first mirror may be positioned below the light-emitting aperture at a pre-determined angle, for instance about three hundred and fifteen degrees, to circuit board 31. A second mirror may be positioned beneath the optical detector, for instance at an angle of about two-hundred and twenty degrees to circuit board 31, such that a substantially 90-degree angle exists between first and second mirrors. A focusing lens may be positioned between the first and second mirrors. Thereby, the light emitted from the LED array may illuminate an assay and then light is reflected therefrom through light-emitting aperture 5, for instance to the first mirror, from the first mirror through the focusing lens to the second mirror, and from the second mirror onto the optical detector. In that respect, the light striking the optical detector may cause the optical detector to generate a measurable voltage. In some examples, the optical detector can output a data stream that can be converted, for example by an on onboard central processing unit, into a series of 128 distinct one-dimensional numeric readings. The 128 readings can be taken multiple separate times and averaged.

In additional examples, a light processor may be coupled to the light source to actuate the light source and provide each light with the appropriate current to generate the desired emission pattern. The light processor may be used to read and store data from the optical detector. The light processor may also be used to adjust the output of an array of discrete light sources such that the emission pattern striking the light detector array has a uniform intensity. The lighting processor may include data storage for the desired light-emission pattern.

Further, the light source may be an LED light source, including a red, green, blue LED device in a single package. For instance, the LED light source for the color sensor can also be three discrete LEDs. Similarly, a single white LED and three discrete photodiodes, with narrow bandwidth responses at the red, green and blue wavelengths, can be used as a detector front-end.

In yet other examples, one LED is used with an optional feedback loop. The feedback loop can use a photodiode to sense light output variation from the single LED. If light output changes, a signal is sent so that an appropriate adjustment can be made, for example, an increase or decrease in current to the LED. Reflectance changes can be the result of the binding of a label, including color particles such as gold beads. Reflectance changes may also be a result of contaminants and interferences in the optical path.

Figure 2:
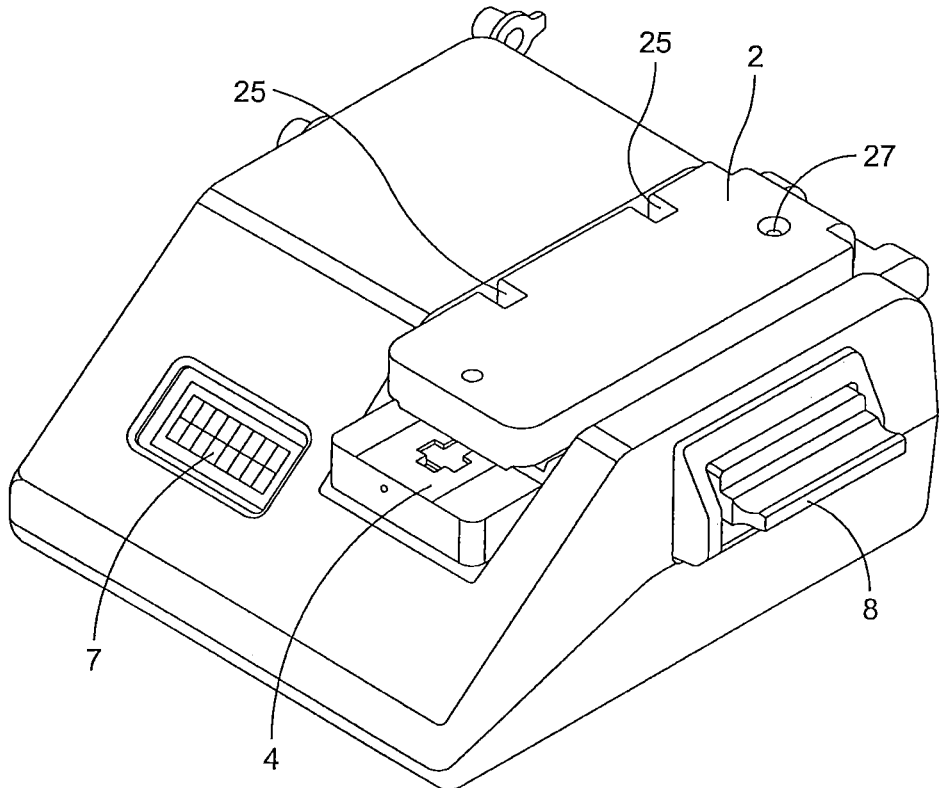
FIG. 2 is a front perspective view of the lateral flow assay system embodiment of FIG. 1, with the hood in a substantially closed position.

As seen in FIG. 2, optical window 8 may be positioned between the assay and reader 100, for instance between a test strip and a sensor. Typically, optical window 8 blocks debris from the assay from contaminating the imaging detector itself, or other system parts used with the sensor, such as lenses and mirrors. In some examples, optical window 8 is clear and includes a handle so that optical window 8 is removable from reader 100 for cleaning. In other examples, the removable optical window may be disposable. In one example, the window material includes clear polyvinyl chloride (PVC) plastic. Window 8 may be mounted on a slide and inserted into reader 100 between cavity 3 and the sensor. The figures show only one removable and cleanable window to block debris, however, other embodiments include additional optical windows covering to protect portions of the optics and/or incubator 102 components.

Regardless of the presence of an optical window, it is possible that dust and debris will infiltrate into reader 100, for example the optical sensor mechanism. To provide an additional cleaning option, air inlet 6 can be provided for compressed air. Air inlet 6 may be covered with a tethered cap 10. In use, clear, optical window 8 is removed, and tethered cap 10 is detached. Compressed air is then blown through reader 100, so that debris collected on, or near, the reader sensor is blown out through the opening previously occupied by window 8.

Some embodiments of reader 100 are programmed with multiple channels, each of which may have separate parameters associated with a related diagnostic test. Each channel selection parameter may include a standard curve, a does-response curve and the like.

Figure 3:
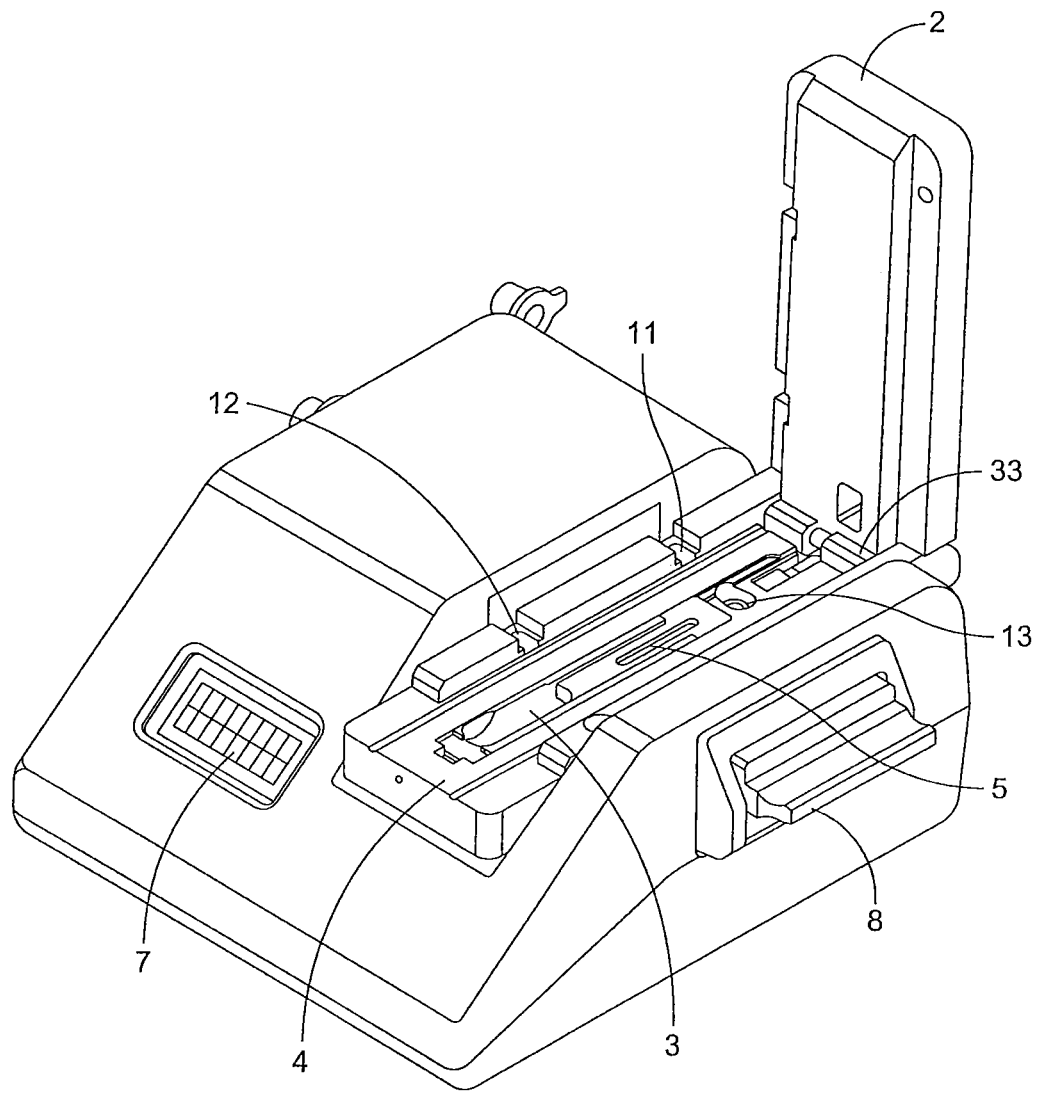
FIG. 3 is a front perspective view of the embodiment of FIG. 1, illustrating examples of cavity and adjustment components.

FIG. 3 shows cavity adjustment fastener 13 in cavity 3, and base adjustment fasteners 11 and 12 in insulated base 4. Openings 25, 26 and 27, in hood 2 allow access to adjustment fasteners 11, 12 and 13, including screws and the like, when hood 2 is in a closed position. In other examples, adjustment fasteners may also be accessed when hood 2 is positioned in an open access position. Typically, cavity adjustment fastener 13 aligns cavity 3 in relation to optics, for instance an imaging detector described hereinafter, so that changes on the assay may be detected.

Figure 4:
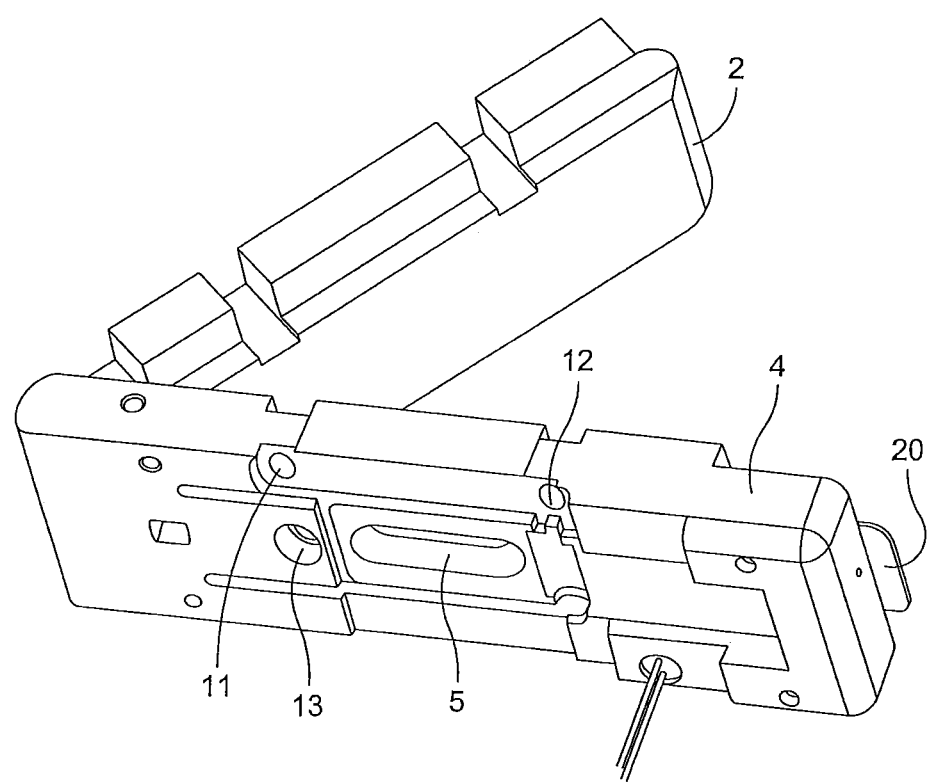
FIG. 4 is an isolated side perspective view of assay base module elements.

FIG. 4 shows one example of insulated base 4 and hood 2 in an opened access position. As shown, the bottom face of base 4 includes openings for cavity adjustment fastener 13, openings for base adjustment fasteners 11 and 12 and light-emitting aperture 5.

Figure 5:
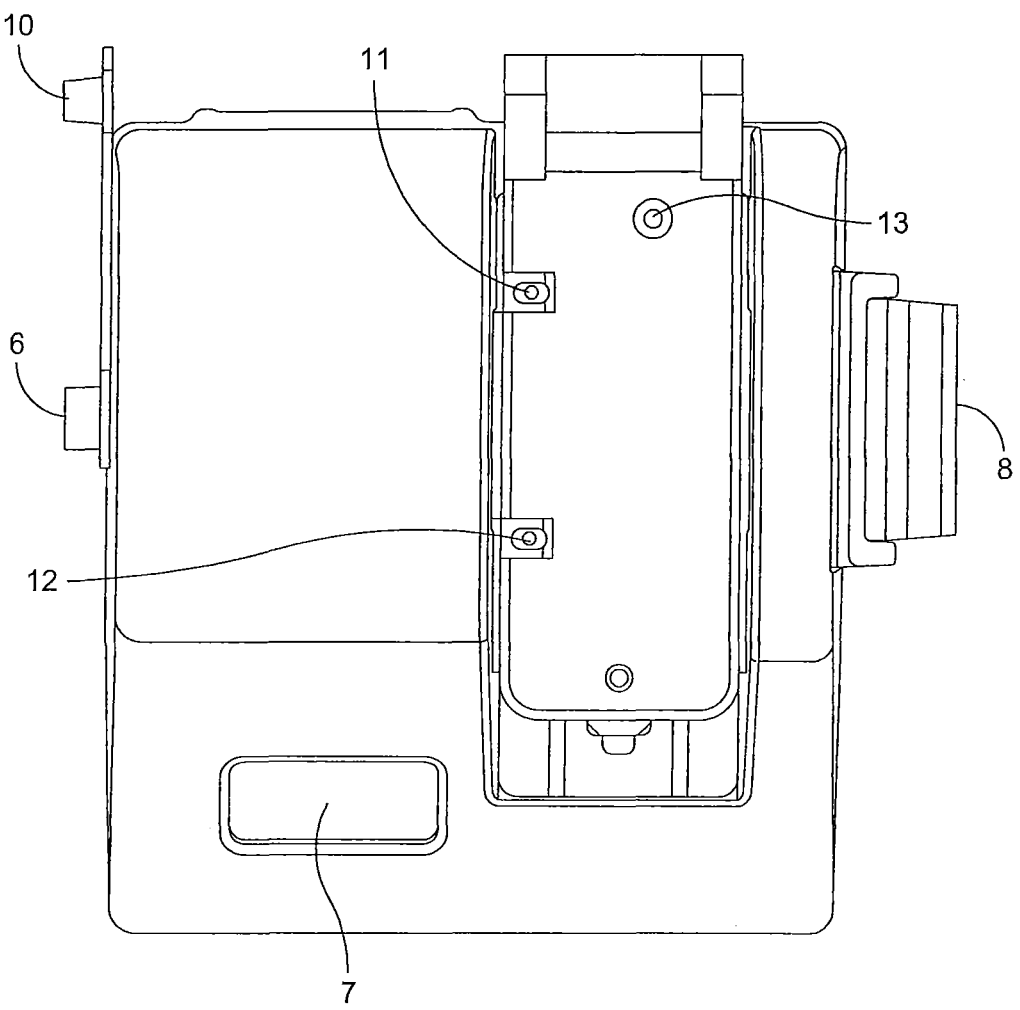
FIG. 5 is a top view of the lateral flow assay system embodiment of FIG. 1 in a closed position.

FIG. 5 shows a top view of lateral flow assay 1 with hood 2 in closed testing position. Window 8 is positioned on the side of the housing to allow the user to remove window 8 for cleaning. As introduced above, air may be inserted through air inlet 6 to further clean debris from optic components.

Figure 6:
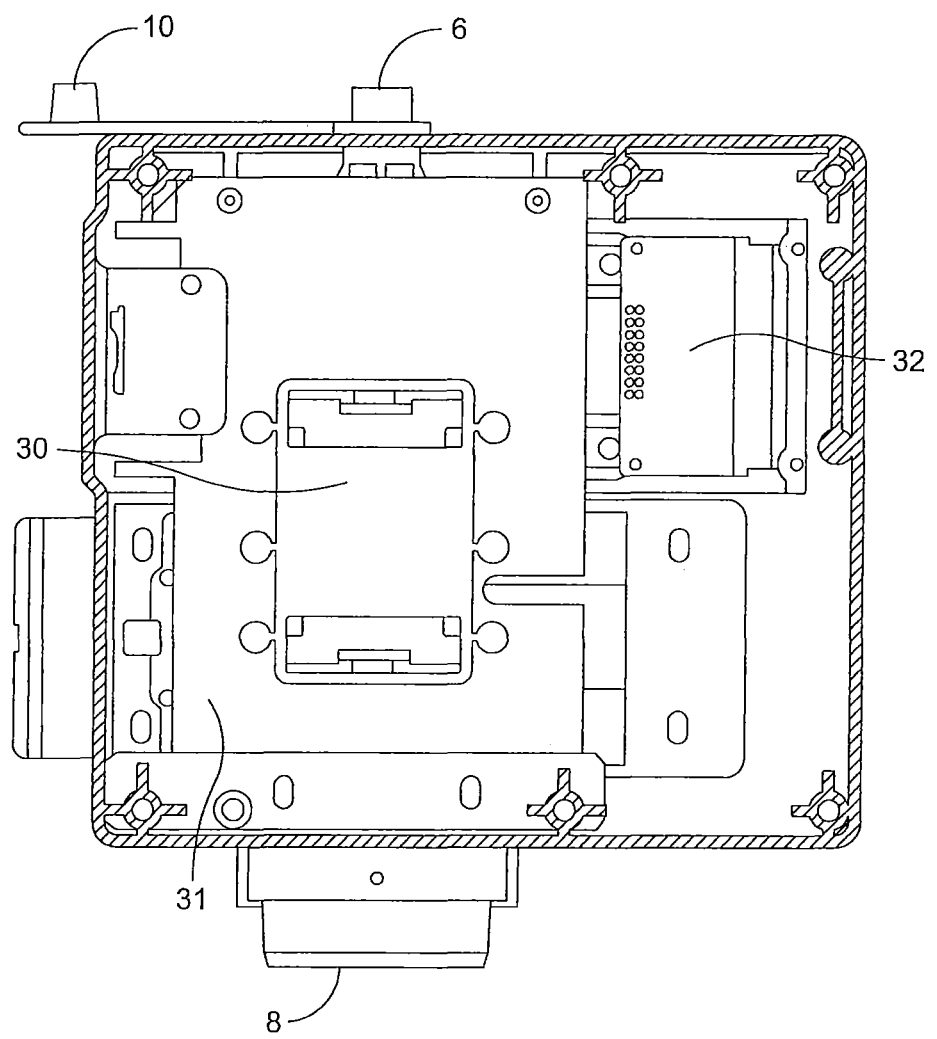
FIG. 6 is a sectional view of the lateral flow assay system embodiment of FIG. 1 taken along lines 6-6, showing circuit board components.

FIG. 6 is a bottom schematic view showing optics board 30, circuit board 31 and display board 32. As shown, LEDs may be mounted on one side of optics circuit board 31. Further, as shown throughout the various figures, lateral flow assay system 1 may include user interface 7. User interface 7 includes an integrated circuit board 31 supporting a display board 32. In one example, user interface 7 allows a user to view flow development. Further, user interface 7 may allow a user to monitor a subsequent flow development after reader 100 has already detected at least one flow development on the assay. Similarly, user interface 7 may display a final test result, including a no-result response.

Figure 7:
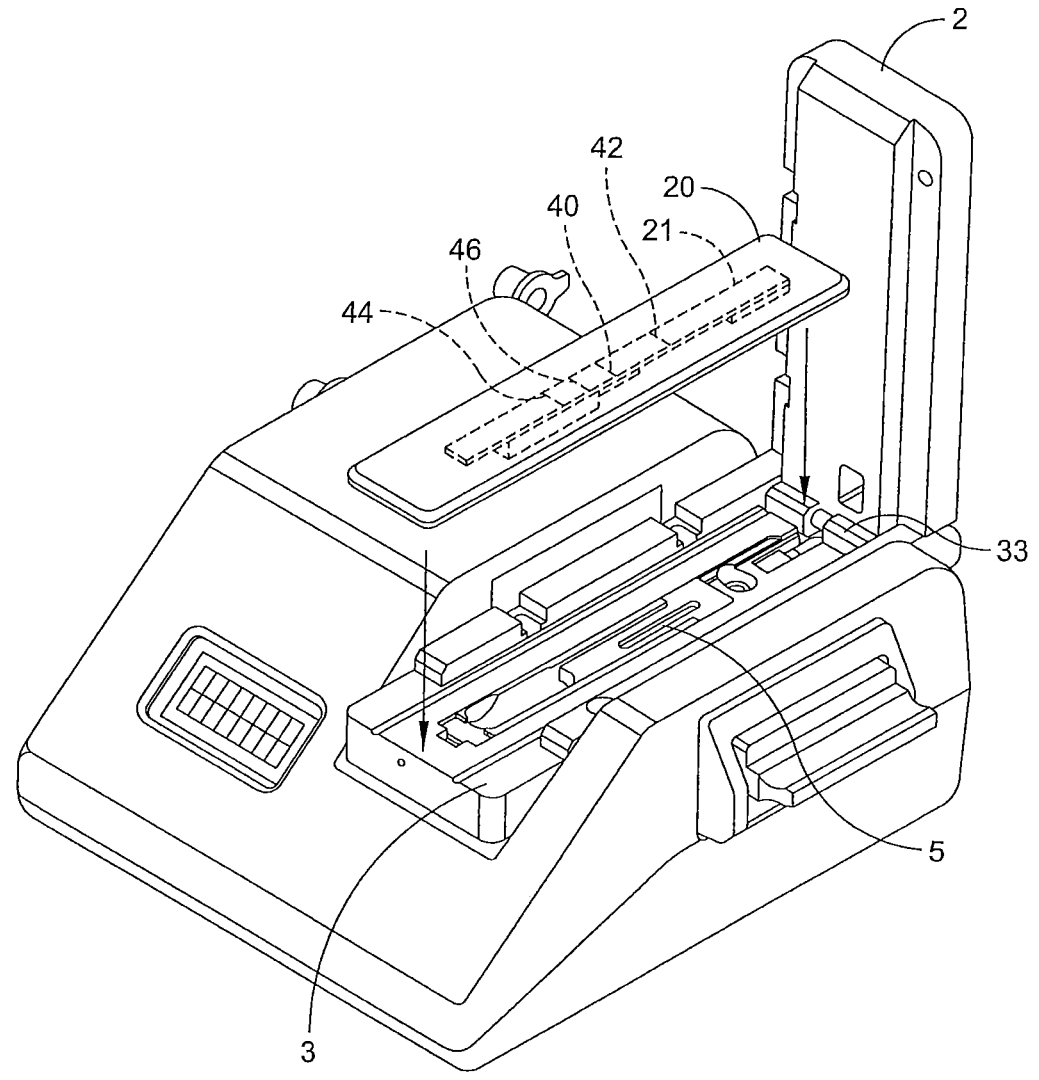
FIG. 7 is a front perspective view of one embodiment of a lateral flow assay system and assay components.

FIG. 7 illustrates one embodiment of hood 2 in open access position with assay 21 secured within test strip enclosure 20, which is adapted to be received by cavity 3. Examples of assay elements for particular diagnostic tests having components useful for embodiments herein include those described in U.S. Pat. No. 7,410,808, issued Aug. 12, 2008; U.S. Pat. No. 7,097,983, issued Aug. 29, 2006; U.S. Pat. No. 6,475,805, issued Nov. 5, 2002; U.S. Pat. No. 6,319,466, issued Nov. 20, 2001; U.S. Pat. No. 5,985,675, issued Nov. 16, 1999 and U.S. patent application Ser. No. 11/883,784, filed Aug. 6, 2007, all of which are hereby incorporated herein by this reference.

Generally, lateral flow assay 21 is membrane-based test device, in which a sample that is suspected of containing the analyte of interest is placed at or near one end of the membrane strip. The sample is carried to the opposite end of the membrane strip by a mobile phase that traverses the membrane strip, for example by capillary action. While traversing the membrane strip, the analyte in the test sample, if any, encounters one or more reagents. The reagents can include binders for the analyte. Binders can be mobile and, therefore, flow with the sample or be immobilized on the test strip as a capture agent. Depending on the test configuration, either the analyte binder, the analyte itself, or some other reagent in the test system, will be captured by the immobilized capture agent and, thereby, produce a detectable signal. The signal can be generated by a label provided within the assay. The detectable signal can be measured, such as by optical reader 100. As shown and described herein, Applicant has unexpectedly discovered the advantage of aligning the assay in an inclined position to minimize impact of in-line sample delivery, including dripage and the like, during mobile phase traversing along the assay.

Assay 21 may include at least one test line 40 in a test zone and at least one control line 42 in a control zone. A theoretical reflectance value may be a comparison between a reflectance value at test line 40 and a reflectance value at control line 42. A pre-set difference between a theoretical reflectance value at test line 40 and a theoretical reflectance value at control line 42 may activate lateral flow assay system 1, including reader 100, to generate a test result. Further, a separate pre-set difference between a theoretical reflectance value at test line 40 and a theoretical reflectance value at control line 42 may trigger an error. Triggering of the error may cause the microprocessor to withhold a test result, including generating a no-result response, or deactivating reader 100 and/or incubator 102. Other embodiments include a comparison between a transmission value at test line 40 and a reflectance value at control line 42.

Rapid result assays are beneficial for any of the in-line testing examples and embodiments shown and described herein. For instance, rapid result assays provide a definitive test result within about fifteen seconds to about one minute, including a definitive test result within about thirty seconds. To increase the speed of a test result, Applicant has unexpectedly discovered optimizing the overlap of a binder application area over a nitrocellulose membrane on the assay allows a definitive test result beneficial for any of the in-line testing processes and embodiments shown and described herein. In one example, a three millimeter overlap of the binder application area over the nitrocellulose membrane optimizes contact surface area between the binder application area and the nitrocellulose membrane to increase flow and release of the sample to meet the thirty second test herein. In particular embodiments, the binder application area can be, for example, POREX® (POREX is a registered trademark of Porex Technologies Corp, Georgia USA), attached to a solid support. In addition, in certain embodiments the nitrocellulose membrane may be optimized to meet the thirty second rapid test herein, for instance the nitrocellulose membrane may ensure sample properly wicks efficiently and rapidly quickly across the membrane to generate the rapid test result analysis shown and described herein. However those skilled in the art having the benefit of this disclosure will recognize additional binder application area materials and/or spacing of the binder application area about the nitrocellulose membrane.

Further, Applicant has unexpectedly discovered optimizing the length of an absorbent pad at the distal portion of the assay enhances capillary action to adjust the speed of sample flow to meet the demands of the in-line testing, for instance the thirty-second rapid test herein. In one example, a thirty-one millimeter length absorbent pad optimizes sample flow along the assay.

A reflectance value on the assay that is inconsistent with the theoretical reflectance value may indicate an inadequate flow in the mobile phase on the assay. For instance, assay 21 may have a flow line 44 with a corresponding theoretical light reflectance measurement. A no-flow development value may be a reflectance value of about 85 on a reflectance scale. Such an inadequate flow may trigger a detectable signal to generate a no-result response. Additional examples include deactivating the lateral flow assay system 1, including deactivating reader 100 and/or incubator 102. In other examples, the flow reference area may include both an intermediate flow reference line 46 with a corresponding theoretical reflectance value and a flow reference line 44.

Similarly, a reflectance value on the assay that is inconsistent with the theoretical reflectance value may also indicate a prior analyte development on the assay. Such a prior analyte development may trigger a detectable signal to generate a no-result response. Further, if the assay is removed prior generating a test result, system 1 may generate a no-response result.

In some embodiments, assays 21 also include a coding reference component with a corresponding testing sequence for lateral flow assay system 1. The coding may be, for example, a color coding, a bar code, an RFID tag or the like, and may be positioned anywhere along the assay so that decoder sensor can decode the reference code, for example on the assay's surface. For instance, in some examples, the coding reference is positioned along the distal end of assay 21. Depending on the type of coding on the test strip, reader 100 may require an integrated decoding sensor for example, a bar code reader, an REED decoder or a color sensor.

Typically, the testing sequence is at least one temperature adjustment parameter within incubator 102 and/or a channel selection of reader 100. Further, the reader test parameter may include an associated feature chosen from a standard curve, a does-response curve and the like. Other embodiments include a variety of testing sequence parameters for the associated diagnostic test being run on the assay.

In some examples, a color matrix, or matrices, reference coding, including a color chosen from red, blue, green and combination thereof, may be associated with a corresponding diagnostic test parameter. When a color coding is used on assay 21, the color can be read by the reader either by a separate optical reading system or the same system that reads the test result. That is, the assay can include a color portion that, after enclosure within the system and test initiation, will be read by the color sensor to determine the reader channel and/or the appropriate incubator temperature. For example, a photodiode with a wide dynamic range of sensitivity to red, green and blue wavelengths can be used as the detector. Red, green and blue LEDs can be used as the light source. Each LED can be turned on sequentially and the detector used to determine the reflectance of each of the colors. A black surface (totally absorbent as containing no color) will produce no reflectance of the given LEDs wavelength and, therefore, the detector will produce low output readings. A white surface will produce maximum reflectance of all three LEDs. Various colors (depending on its content in the surface measured) will produce output from the detector at varying levels.

Such color sensor component may be configured as a separate sensing component within reader 1, or depending on the sensor used to read the test strip result, a singular component that detects both development on the test strip and color coding. In various examples, assays may be coded with a color that defines the test being run. For example, a red color can indicate a test strip to be used to detect beta-lactam antibiotics. Various matrices can also be delineated by the color system. In the red example, after system 1 detects the red color on the test strip, reader 100 and/or incubator 102 may be automatically configured for that specific assay 21, for example by temperature adjustment of incubator 100 and selection of appropriate reflectance test parameters within reader 102. Therefore, in some embodiments, system 1 may an integral diagnostic test unit that is triggered by specific reference codings on the assay.

In other examples, the coding reference may comprise a radio frequency identification (RFID) tag. Such radio frequency signal transmits a signal from the tag to a decoding RFID sensor module. This signal can be used to start the analytic testing sequence, event, channel, temperature or the like in the reader and/or incubator. Similarly, the reference coding may be a bar code, wherein the bar code is placed on the assay and a bar code reader decodes the reference coding and associated testing sequence information.

Figure 8:
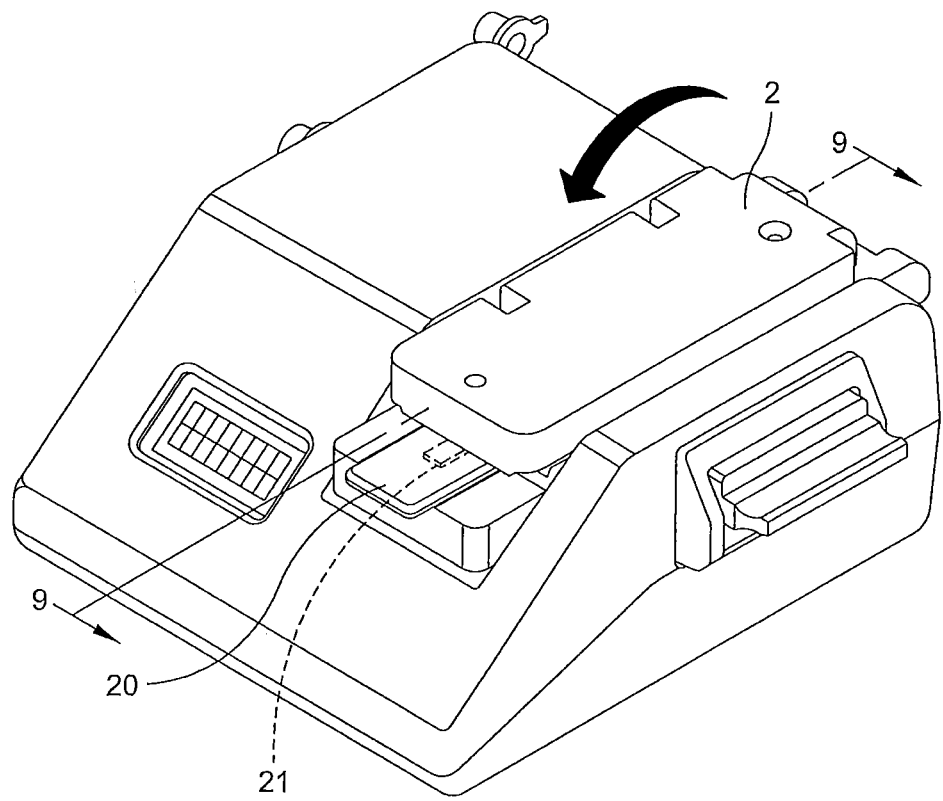
FIG. 8 is a front perspective view of the embodiment of FIG. 7 in a closed position.

FIG. 8 shows assay 21 and assay enclosure 20 positioned within the reader, with hood 2 in a closed position. As shown, hood 2 is pivoted down in a closed testing position, wherein a sensor in the reader is in an optical alignment with assay 21 to generate a test result or a no-result response.

In the closed testing position, incubator 102 may incubate assay 21 in an incubation environment. For instance, incubator 102 may heat and/or cool assay 21 to provide the proper incubation environment for a corresponding assay and diagnostic test. Typically, incubator 102 is in communication to the cavity 3 and is capable of maintaining a consistent temperature within cavity 3 either by heating or cooling at a pre-defined rate. In some examples, incubator 102 includes insulated base 4. In other examples, incubator 102 incubates removable assay module 104, as described hereinafter. The incubator may be a temperature adjustable incubator. In these examples, the temperature adjustable incubator may include a temperature control. In additional embodiments, the temperature adjustable incubator may allow for localized temperature changes.

Incubator 102 may include a heater. The heater may be a ceramic heater, a resister heater element and the like. Typically, cavity 3 is designed to be small so that the heater need only draw minimum current. In that way, heating only essential areas and providing insulation around those areas minimizes power requirements. Use of various heating algorithms can be useful. For example, a proportional integrated derivative (PID) can be used. In other examples, incubator 102 may compensate for localized temperature variations from the selected target temperature, for instance a target temperature according a corresponding testing sequence. Incubator 102 may also compensate for localized temperature variations with an analog, proportional control circuit. In other examples, incubator 102 may also compensate for localized temperature variations with a digital control circuit, for instance by utilizing a PID algorithm or a PID controller. Further, those of ordinary skill would recognize that PI, PD, P or I controllers, and/or algorithms, do not preclude any of the inventions herein. For instance, temperature adjustable incubator may include a digitally controlled potentiometer to allow the microprocessor selection of temperature. In other examples, algorithms are particularly useful when test results are affected by small temperature variations. Embodiments include incubator control systems that eliminate the need for manual adjustment by use of embedded, digital temperature sensors and digital potentiometer that provides both accurate temperature reporting and a mechanism by which a micro-controller can adjust a stand-alone, analog, incubator control circuit.

In additional embodiments, cooling might be advantageous to reduce the incubation environment temperature, for example to stabilize the environment of a test medium and/or sample prior to incubation.

Figure 9:
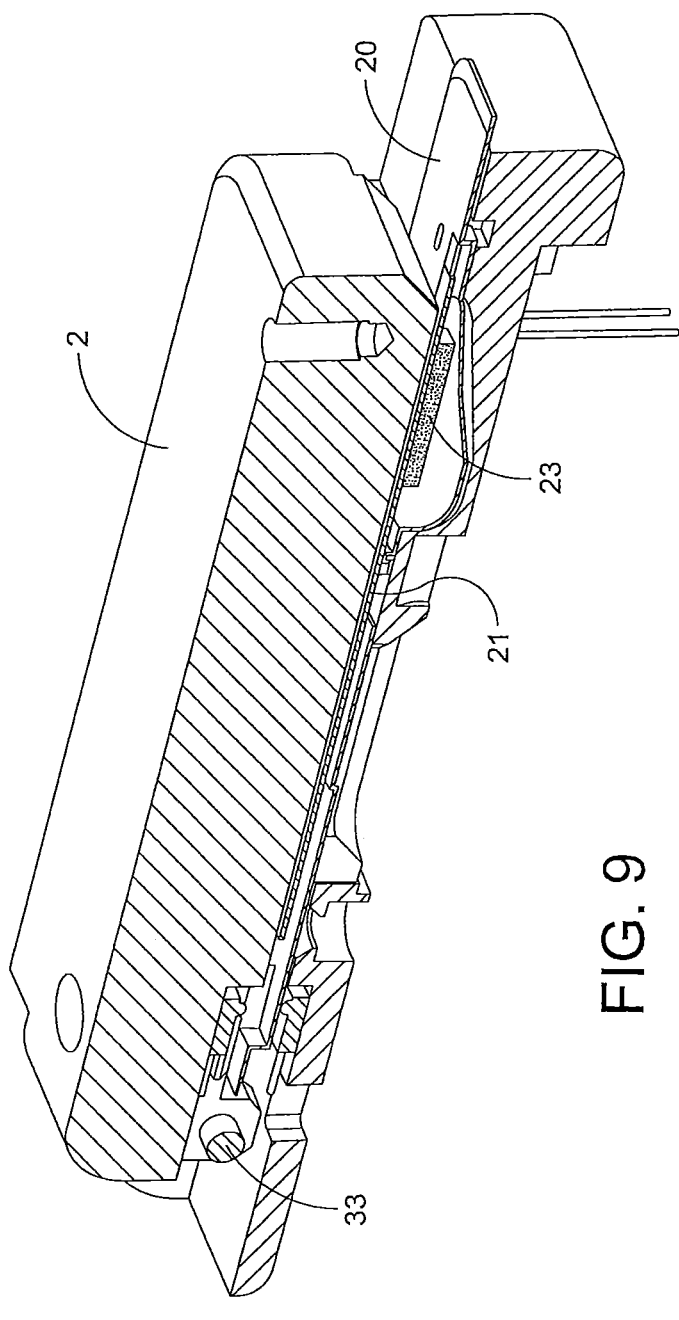
FIG. 9 is a partial cross-section of one example of the embodiment introduced in FIG. 7 taken along 9-9.
Figure 10:
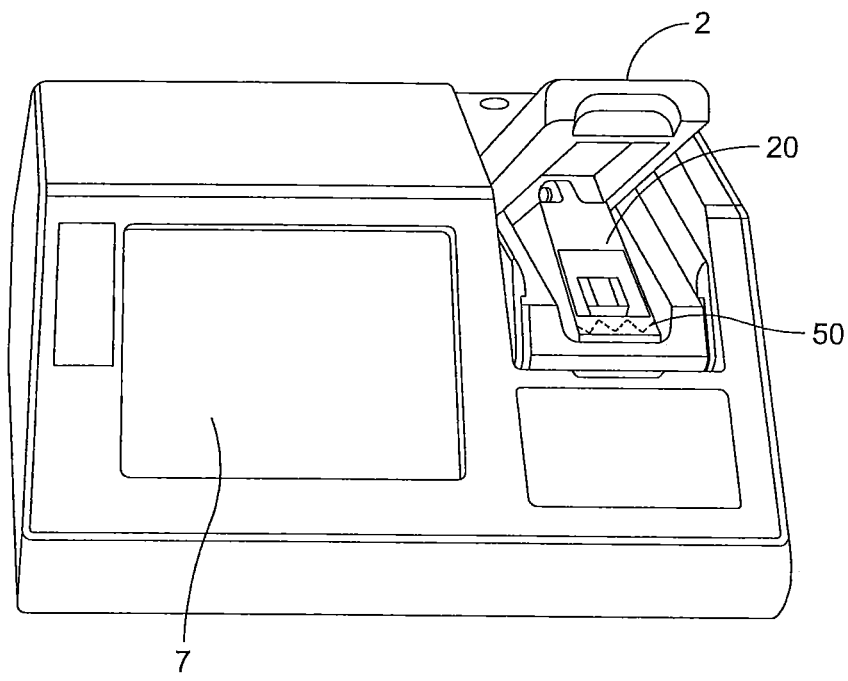
FIG. 10 is a front perspective view of one embodiment of a lateral flow assay system and assay components.
Figure 11:
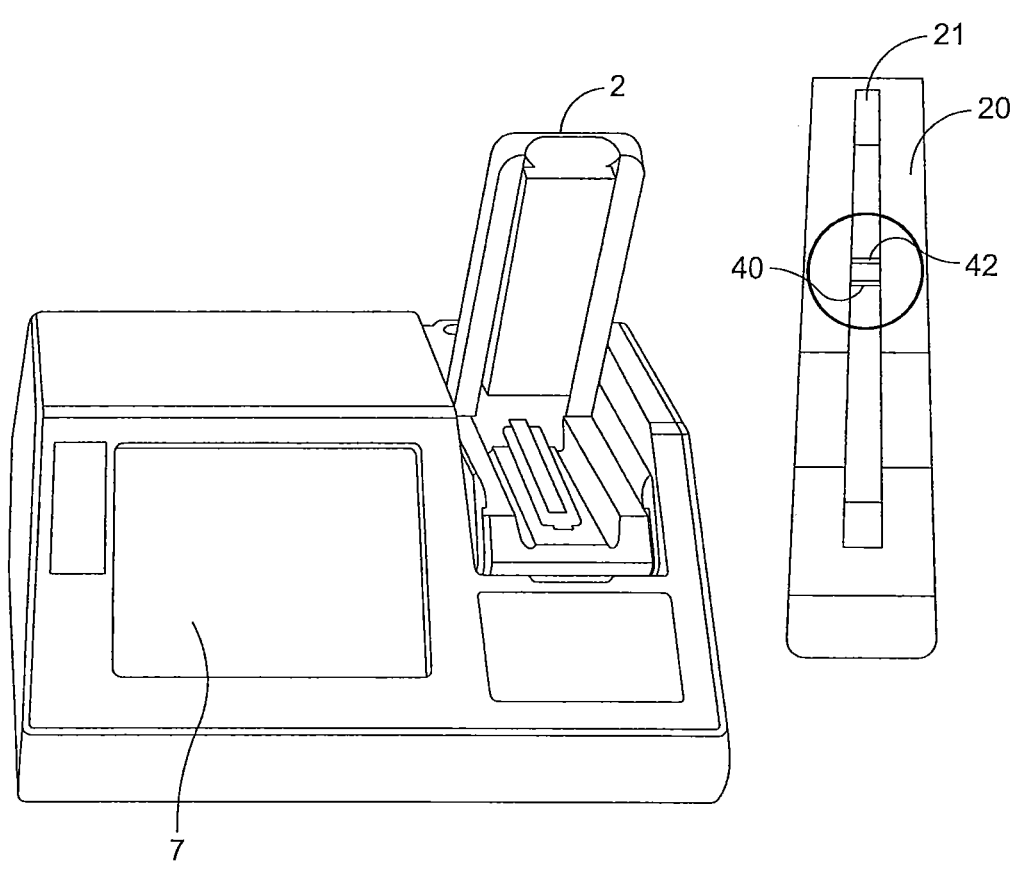
FIG. 11 is a front perspective view of one embodiment of a lateral flow assay system and assay components.

As shown in FIG. 9, test strip 21 may include a first end having a sample absorbing material 23. Further, as introduced in FIG. 10, test strip 21 may have a peel strip 50 to introduce sample onto sample absorbing material 23. Peel strip 50 may include a peel tab at one end of peel strip 50 to facilitate movement of the peel strip 50. Sample absorbing material 50 may be sized and configured to receive about 0.1 to about 1.0 mL of a fluid. Further, sample absorbing material 50 may be composed a dry cellulosic material. Other embodiments include other materials of sample absorbing material 50.

Figure 14:
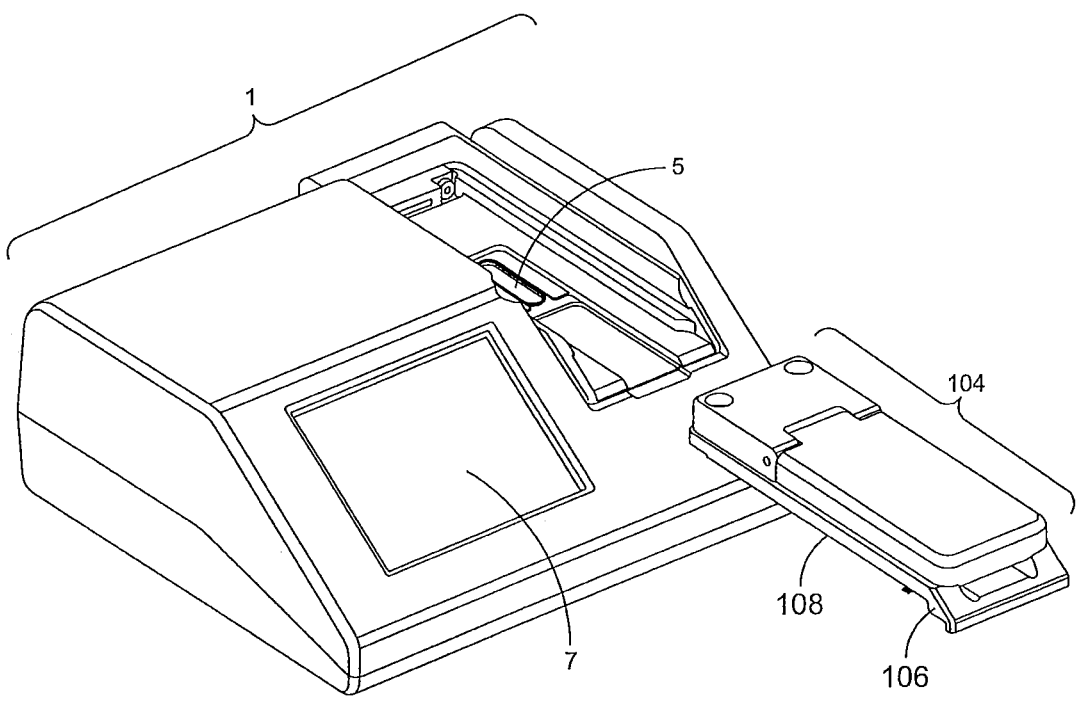
FIG. 14 is a front perspective view of one embodiment of a lateral flow assay system having a removable assay module.

Typically, assay 21 also includes an opposed second end having a reactor detector material. Assay 21 may support a releasing area having a mobile phase receptor for the at least one analyte. Further, assay 21 may be sized and adapted to be enclosed within test strip cavity 3. Similarly, assay 21 is typically sized and adapted to be enclosed, for example enclosed tightly, within an assay cavity 3 of a removable incubation module 104, as seen in FIG. 14. Typically, assay 21 is adapted for selecting the detection of a diagnostic test group chosen from an antibiotic analyte, toxic analyte, analyte class, a combination thereof and the like.

Reader 100 may include a sensor to monitor a test progress, for example on a lateral flow assay, and/or determine a test result from the lateral flow assay. The sensor is positioned relative to assay 21, so that a change on assay 21 can be detected by the sensor. Typically, the sensor is activated when the lateral flow assay is both positioned within cavity 3 and exposed to the consistent temperature within cavity 3 from incubator 102. For example, the sensor can be activated by closing hood 2 that encloses cavity 3. The sensor may include an optical detector and a microprocessor. Typically, the optical detector is aligned in an optical path with the assay and is adapted to acquire an image detection on the assay and is performing a continuous image detection acquisition of the assay.

The sensor may be a single photodiode, multiple photodiodes, a linear photodiode array, a charged couple device, a complementary metal oxide semiconductor and a combination thereof. Therefore, at the same time as incubation and flow, or before, or after incubation and flow is complete, the optical sensors can monitor the assay and compare optical readings, such as reflectance and/or transmission readings, to determine various aspects including sample flow, interference with the optical path such as by debris in the optical path, line development and test result. When the assay and line development falls within preset parameters, the test can continue to completion and provide a final result. Checking of the assay by the optical sensor prior to test completion can provide the user with additional confidence that the test was processed properly.

Typically, the output may be a voltage, current or a digital output proportional to light intensity as determined by signal conditioning circuitry. Sonic examples of reader 100 include the TSL 12T and TSL 13T sensors available from TAOS (Texas Advanced Optolectronic Solutions). The TSL12T and TSL13T sensors are cost-optimized, highly integrated light-to-voltage optical sensors, each combining a photodiode and a transimpedance amplifier (feedback resistor =80 Mn and 20 Mn respectively) on a single monolithic integrated circuit. The photodiode active area is 0.5 mm×0.5 mm and the sensors respond to light in the range of 320 nm to 1050 nm. Output voltage is linear with light intensity (irradiance) incident on the sensor over a wide dynamic range.

In some examples, the microprocessor may be in communication with the optical detector, and in particular with the sensor. In other examples, the optical detector outputs to other logic means. Further, the microprocessor may be adapted to signal the optical detector to perform continuous image detection of the assay to generate the diagnostic test result. The microprocessor may include, or have associated, memory to store information corresponding to an imaging parameter. The memory may include instructions for monitoring a pre-test analysis on the assay and for generating a diagnostic test result on the assay.

In some embodiments having assays with coding references, as discussed herein, the optical detector may have a decoding ability to decode a reference code on the assay. Thereby, the decoding sensor may thereby active a corresponding diagnostic test in reader 100. For instance, the decoding sensor may activate a corresponding channel in a multichannel reader 100 and/or activate a corresponding incubation temperature profile within incubator 102

The decoding sensor may be a color sensor. For example, the color sensor may be a photodiode with sensitivity to wavelengths chosen from red, blue, green and a combination thereof. In such an example, a color reading an arrangement of photodiodes, each with a specific color filter, is used as the decoding sensor and a white LED (which provides a wide spectrum of light through the 3 bandwidths (lied, Green and Blue)) is used as the light source. When the LED is turned on, the output from each of the photodiodes is obtained to determine the reflectance of that specific color. The decoding sensor may also be an RFID reader or a bar code reader.

Although reference is often made herein to optical reflectance, and optical reflectance readers, a variety of readers may be usefully employed including, for example, transmittance reader, fluorometers, luminometers, bar code readers, radiation detectors (such as scintillation counters), UV detectors, infrared detectors, electrochemical detectors or optical readers, such as spectrophotometers, charged coupled device (CCD) or complimentary metal oxide semiconductor (CMOS) can be used as an image sensor. An optical reflectance reader can be programmed to analyze the test strip through two-dimensional readings, rather than through the one dimensional, 1×128, readings. For example, a 5×128 or 512×492 matrix of "pixels," Such a 2-dimensional reading widens the reflectance capture area to capture reflectance directly from the sides of the test strip.

In other examples, a transmittance reader, such as an ultraviolet Visible Near-Infra red (UV-Vis-NIR) spectroscopy may provide a characterization of the absorption, transmission, and/or reflectivity of the assay. For instance, such an analytical technique may measure the amount of light absorbed on the assay at a given wavelength. Those of ordinary skill in the art would appreciate that a molecule, or part of a molecule, can be excited by absorption. Typically, organic chromophores which absorb strongly in the UV or visible portions of the spectrum nearly always involve multiple bonds, such as $C=C$, $C=O$ or $C=N$. This molecular excitation energy may be dissipated as heat, for instance kinetic energy, by the collision of the excited molecule with another molecule, e.g., a solvent molecule, as the molecule returns to the ground state. In other embodiments, the excitation energy may be dissipated by the emission of light in via fluorescence. Regardless of the process, an excited molecule may possess any one of a set of discrete amounts of energy, for instance as described by the laws of quantum mechanics. In examples herein, the major energy levels may be determined primarily by the possible spatial distributions of the electrons, and to a lesser extent by vibrational energy levels, which arise from the various modes of vibration of the molecule.

Therefore, in particular examples herein, absorbance measurements may be determined by the concentration of a solute on the assay. For instance, the progress of such a chemical reaction may be followed using a spectrophotometer in reader 100 to measure the concentration of either a reactant or a product over time. In other examples, a transmission spectroscopy may be used for solid, liquid, and gas sampling. Typically, light is passed through the assay and compared to light that has not. The resulting spectrum may depends on the pathlength or sample thickness, the absorption coefficient of the sample, the reflectivity of the sample, the angle of incidence, the polarization of the incident radiation, and, for particulate matter, on particle size and orientation.

Figure 12:
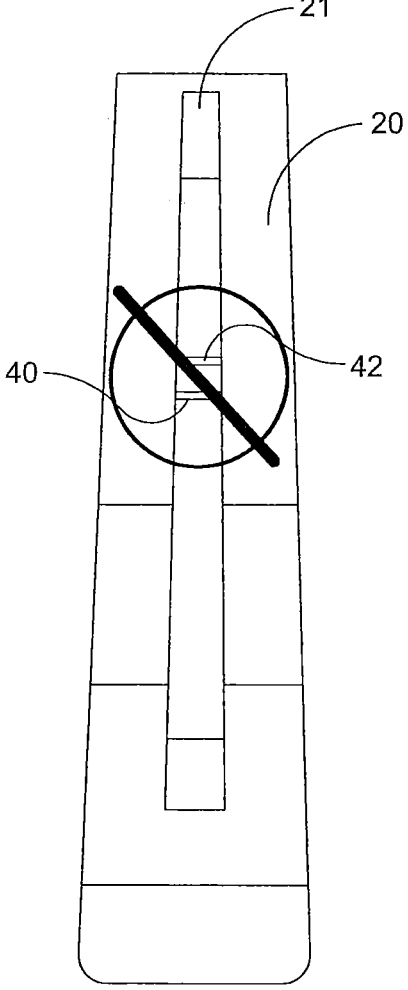
FIG. 12 is an isolated view of the assay illustrated in FIG. 11, showing one example of a prior analyte development before testing triggering an error.

In some embodiments, the sensor monitors assay 21 for prior analyte development before generating a test result. As shown in FIG. 12, prior analyte development on test line 40 and control line 42 indicates an error. For instance, assay 21 may have a theoretical reflectance value that is a comparison between a reflectance value at test line 40 and a reflectance value at control line 42. A reflectance value on assay 21 that is inconsistent with the theoretical reflectance value may indicate a prior analyte development on assay 21, including a pre-run assay, contaminated assay or the like. The prior analyte development may trigger a detectable signal to generate a no-result, for instance a no-run, response and/or deactivate assay system 1. Other outputs may be indicative of the detected condition and are also within the scope of these inventions.

Further, the sensor may monitor flow development along assay 21 to assess whether an inadequate sample volume has been applied to assay 21, or that excess volume has been applied. For instance, prior to determining the test result, the sensor may monitor the flow progress on assay 21 along flow line 44. In other examples, the sensor will monitor flow progress at both flow line 44 and along the assay, for instance at intermediary flow line 46. The sensor may be configured to sense whether an adequate flow of a reagent occurred on assay 21, while assay 21 was within cavity 3, and/or whether one or more lines, i.e. reflectance or transmission values, were present on assay 21 prior to contact of assay 21 with the sample to be tested.

In addition, the sensor may be configured to detect whether dirt/debris is contaminating the optical path. For instance, the sensor may monitor the optical path for interference such as by debris. To determine that a test has run properly, or that the assay is free of dirt/debris, predetermined optical measurements, such as reflectance values or transmission values, may be stored electronically. The preset values, or preset parameters, can include a theoretical reflectance, or transmission, value from an unused assay (prior to receiving reagents). Preset values may also include values may be one or more theoretical test lines and/or one more theoretical control lines on the assay, and may also include a difference between the theoretical reflectance values for the one or more control lines and the theoretical value for the one or more test lines.

Figure 13:
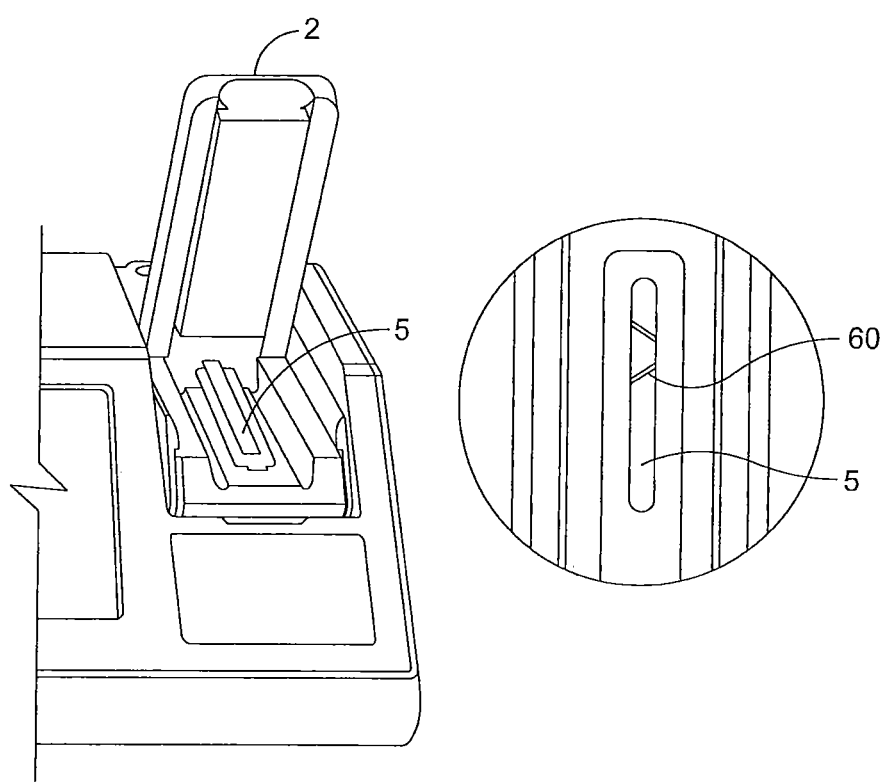
FIG. 13 is a front perspective view of one embodiment of a lateral flow assay system with debris on the imaging detector.

FIG. 13 shows one embodiment of lateral assay system 1, with debris 60 over light aperture 5. In use, a reflectance value on an assay that is inconsistent with the theoretical reflectance value may indicate a contaminated optical path, such as debris 60 as shown here. Lateral assay system 1 may be adapted to generate a no-run response and/or deactivate reader 100 and/or incubator 102 when the sensor detects such an aberration.

In other examples, the optical detector may monitor at least one pre-test parameter after the optical detector has already acquired at least one image detection on the assay. Similarly, optical detector generates a test result from assay 21, for instance by a comparison between at least two lines on the assay, for examples lines 40 and 42 of the test strip depicted in FIG. 7. As indicated above and in the incorporated references, optical detector may compare changes in reflectance values of two lines on the assay, for instance at least one test line 40 and at least one control line 42.

Particular embodiments include configuring the lateral flow assay system to allow concurrent incubation and reading of assay 21. The combination allows sensors to be used to detect not only test results, but also to check parameters that might indicate whether or not flow has occurred on the assay and that such flow caused a proper test result. That is, while sample, including the potential analyte, or analytes, of interest, is flowing on assay 21 and binding is occurring in a mobile phase and on assay 21, the assay is being incubated. By combining reader 100 and incubator 102 into such an integral diagnostic unit 1, results can be achieved quicker than when assays, such as test strips or other test medium, are incubated in one device and then moved to a separate device for reading. For instance, speed-to-result can be enhanced, for example to as little as less than about 60 seconds or even less than about 30 seconds. Generally, such a combined system can be dynamic, sensing changes in the assay as they occur by looking for areas of decreased reflectance and/or transmission anywhere on the unused or not-fully developed assay.

A level of protection is provided to prevent pre-run assays from being read (for example, reader 100 will determine if line development, for instance at flow line 44, intermediary flow line 44, test line 40 and/or control line 42 occurred prior to the time when sample flow could have reached such line) and to prevent incorrect readings caused by debris, or similar interference with system optics.

Various triggers may initiate assay analysis of system 1. For example, closing of hood 2 may initiate test operation, including optical measurement. Alternatively a separate switch can be used to initiate test operation after hood 2 is closed. In either case, a first reading may determine whether a proper assay is correctly position in the system. If assay 21 is detected, a reading sequence is initiated. For example, optical measurement, such as to detect light reflected off assay 21, can utilize values, such as average reflectance values, in certain areas of assay 21. Initially system 1 may analyze the assay to determine if the optical path is clear of interference, such as from debris. Debris can be in any number of locations in the optical path including on assay 21 or assay container 22. Concurrently with analyzing the optical path for debris, or subsequent thereto, the system can analyze the assay to determine if line development has already occurred. That is, whether a proper assay has been inserted into cavity 3. For example, test strips configured to develop within certain areas, such as a test line and control line, should have no development in those areas before the analyte and mobile phase have had adequate time to reach them.

In some examples, livres configured to develop a change in reflectance, and/or transmission, when contacted by reagents and sample should not develop until flow of sample and reagents has arrived and binding has occurred. That flow will not have arrived at the time of an initial, for example about three second, read. As such, if line development is detected at the initial assay analysis, then an error message will be delivered to the user and further readings, for example further optical measurements, can be aborted. In this way, this mechanism can detect the use of pre-run (known negative) assay or pre-marked assays. Generally, when reflectance is reduced on an unused assay, either by the presence of line development or other darkening of the assay away from baseline, the reduction in reflectance can inform the user that something has occurred either on the assay or in the optical path, so that the result should not be accepted.

After initial optical readings are found satisfactory and appropriate reader parameters and incubator temperatures are selected, either manually or automatically, further optical readings, for example approximately fifteen seconds after sample has been applied, can be used to determine whether adequate flow has occurred. For example, optical readings can determine whether or not reagents have flowed between a sample application region and a downstream line such as a test line.

The presence of label, such as colored particles, for example gold sol beads, flowing in the mobile phase, and the resulting reflectance changes on the assay between the sample application area and a first test line, can inform the user that flow is occurring and return an error message if no flow is detected. An assay lacking predictable reflectance changes might either have had no sample flow, or inadequate sample flow. Certain measurements can also indicate whether excessive flow has occurred, as in the case where too great a volume of sample has been applied to a test strip and possible reflectance change due to reagents is overwhelmed by the excessive sample volume. Reflectance changes between the sample application area and result detection areas, such as test line and control line, can be temporary and disappear as the mobile phase flows. If optical measurements are taken such temporary/non-permanent changes can be detected.

If an assay, including a test strip or other assay type, has passed the preliminary readings, system 1 may initiate readings to generate a test result. For example, after approximately thirty seconds test line and control line analysis can begin. When there is enough differentiation, for example percent reflectance difference, between the test and control, a result can be provided. Typically, negative results and more extreme results can be provided sooner and results closer to threshold levels will take longer. For example, in the case of a test in which the reflectance value on the test line relates inversely to the amount of analyte, if the test line reflectance is reduced to a certain level then a negative result can be called. In some examples, if hood 2 is opened while reader 100 is reading the assay, a signal may generate a no-result response.

Reader 100 and/or incubator 102 may be powered by a power source. In some examples for on-site analysis, for instance in rugged environments, the power source may be a vehicle battery. Further, reader 100 may be in communication with an onboard vehicle system.

As introduced in FIG. 14, lateral flow assay system 1 may include removable assay module 104 to be removed from system 1 and cleaned from debris. Typically, removable assay module 104 includes a similar assay cavity as described above, to align assay 21 with optics of reader 100 while in a closed testing position. In some examples, the assay is a lateral flow test strip and the assay cavity within removable assay module 104 is sized to receive the lateral flow test strip.

As discussed above, removable assay module 104 may include a hood. The hood may enclose the assay in a closed testing position and be opened to clean away debris in an open maintenance position when removable assay module 104 is removed from system 1. In some examples, if the hood of removable assay module 104 is opened while reader 100 is reading the assay, a signal may generate a no-result response. Further, removable assay module 104 may have a bottom face having a window 108 to slide in between reader 100 and the assay in a manner so that at least one light aperture 5 aligns with the assay in a closed testing position. Window 108 may be removable and cleanable as discussed above, and further the bottom face may include holes to receive an adjustment fastener to secure removable assay module 104 into an optical alignment with reader 100. In other examples, bottom face 108 may include engagement lip 106 to position bottom face 108 securely with reader 100.

Figure 15:
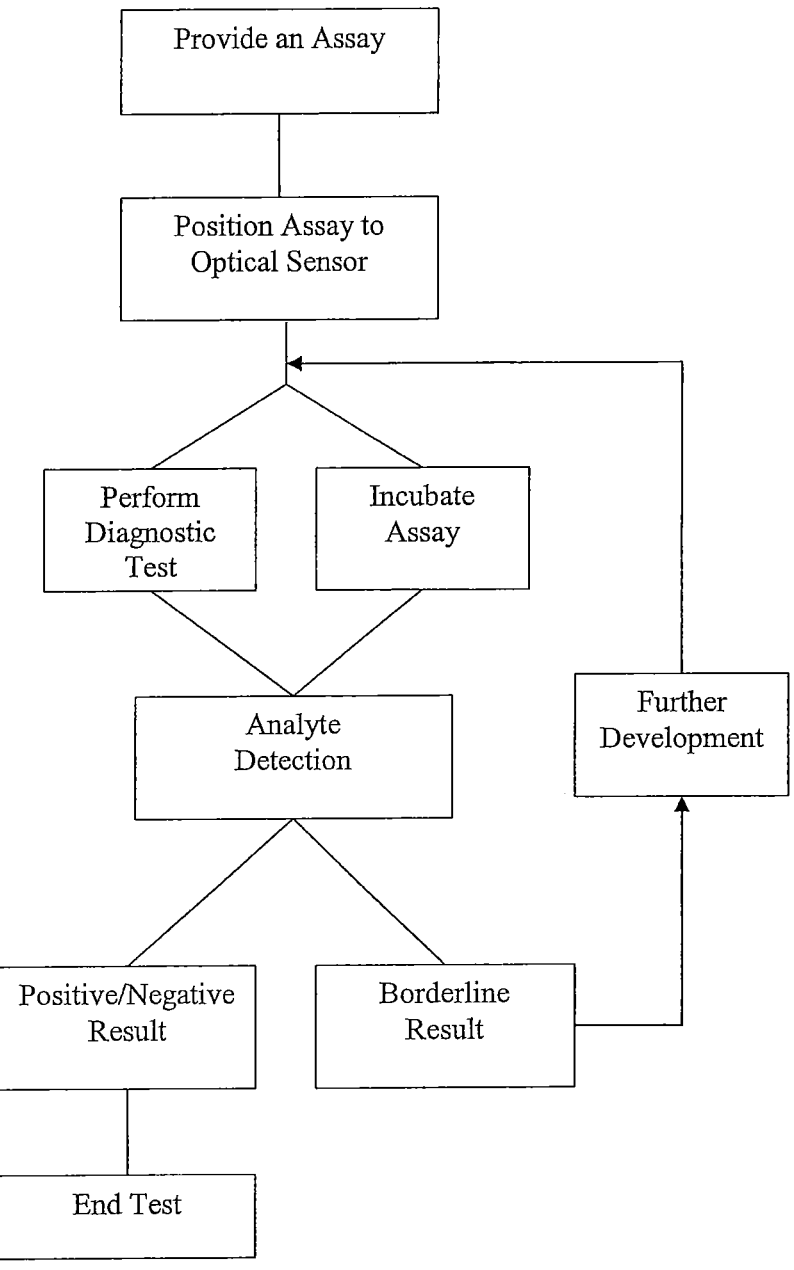
FIG. 15 is a flowchart of a diagnostic testing sequence of one embodiment of the disclosure.

FIG. 15 illustrates a flowchart of one testing sequence of the combined reader 100 and incubator 102. As shown in FIG. 15, the diagnostic test may begin with providing an assay 21. For instance, providing an assay 21 may include adding a test sample to a test medium, such as a lateral flow test strip, e.g. including any of the test strip embodiments previously shown or described. Typically, the test medium is configured to provide a detectable test result after, and/or during, incubation with the test sample. Next, the assay 21 is positioned to an optical sensor, e.g. including any of the sensor embodiments previously shown or described. The assay 21 then undergoes diagnostic testing concurrently with incubation, as described herein for the detection of the presence or absence of a particular analyte or plurality of analytes.

In some examples as shown in FIG. 15, a clear positive or clear negative test result, i.e. a definitive presence or definitive absence detection of an analyte will end the testing sequence. However, a borderline result, i.e. a non-definitive presence or a non-definitive absence result, will trigger a further development in the testing sequence to achieve the definitive test result. A definitive test result may include a variety of results and testing sequences, depending on the particular diagnostic application. For instance, a definitive test result may be determined when the difference between the reflectance value of the control line 42 and the reflectance value of the test line 41 reaches a predetermined parameter. Therefore, the predetermined parameter may be any of the theoretical reflectance values described herein, and for example the predetermined parameter is typically a comparison between a reflectance value at test line 40 and a reflectance value at control line 42. In other examples, a definitive test result may occur when the difference between the reflectance value of the control line 42 and the reflectance value of the test line 40 reaches a predetermined parameter and the reflectance value on the control line 42 achieves a predetermined level. In this example, the definitive test result confirms that the test was fully developed. In yet another example, a definitive test may be achieved when the control line 42 and/or the test line 40 individually obtains a predetermined parameter as described herein.

As shown in FIG. 15, a preliminary non-definitive test result leads to further development, i.e. continued optical sensing, and in many examples concurrent incubation. In exemplary embodiments, further development is performed until a clear positive or clear negative test result is detected. This definitive presence or definitive absence detection of an analyte typically ends the testing sequence. However, those of ordinary skill in the art having this disclosure will recognize other examples include a variety of further development testing sequences.

Figure 16:
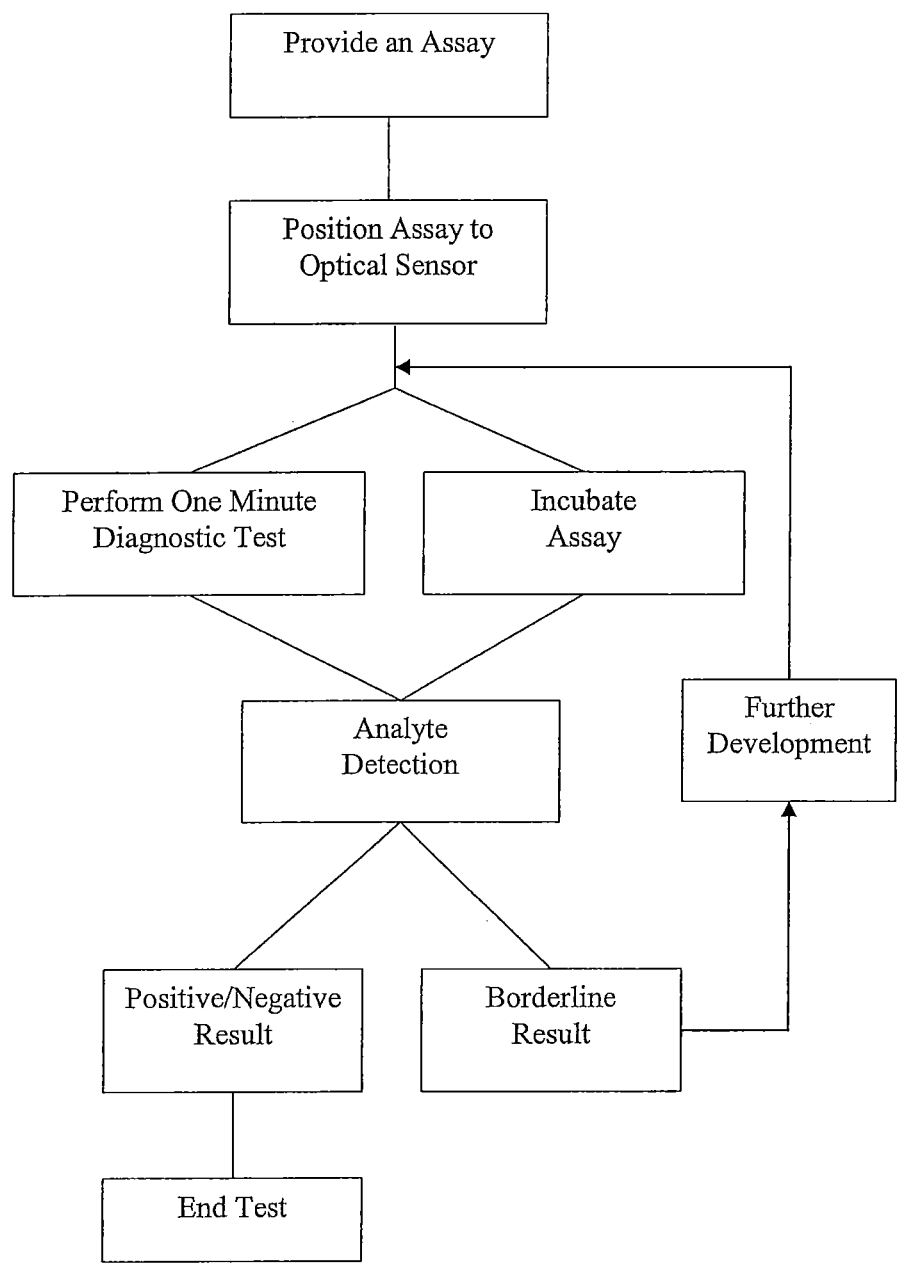
FIG. 16 is a flowchart of a one minute diagnostic testing sequence according to one embodiment of the disclosure.

FIG. 16 illustrates a flowchart of another testing sequence. As shown in FIG. 16, the diagnostic test sequence is similar to the steps introduced in FIG. 15; however, the reader 100 is programmed to perform about a one minute diagnostic test read. Other examples include about thirty seconds, about two minutes and similar reads. Again, a clear positive or clear negative detection of an analyte will end the testing sequence, but a borderline result will trigger further development in the testing sequence. In some examples, the second, or additional, diagnostic testing, e.g. any of the testing previously described herein, may also he one minute diagnostic reads. However, those of ordinary skill in the art having this disclosure will recognize other examples include a variety of testing lengths and sequences to meet a particular application or test result.

Figure 17:
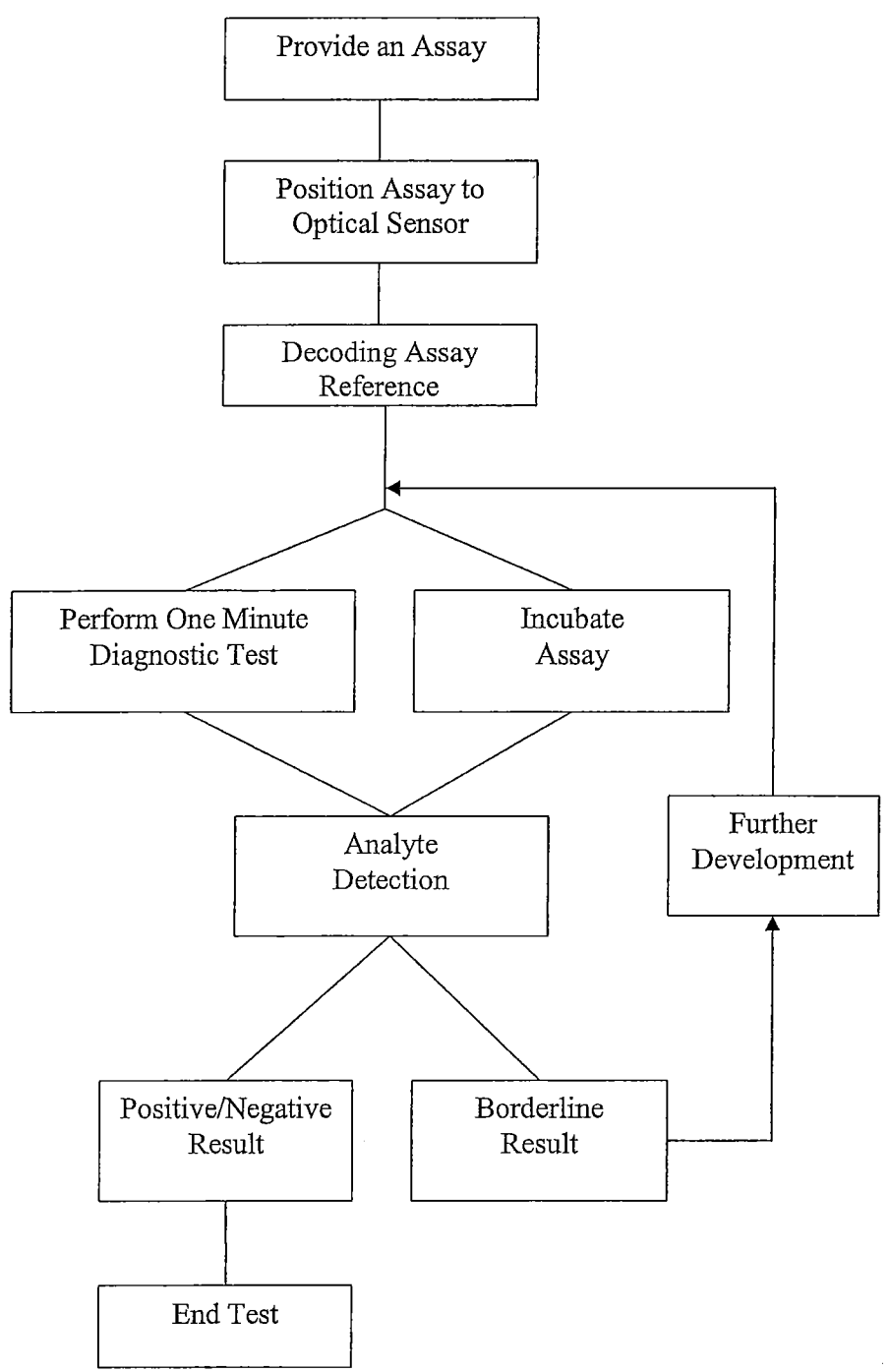
FIG. 17 is another flowchart of a diagnostic testing sequence according to one embodiment of the disclosure, including the step of decoding an assay reference.

FIG. 17 shows another testing sequence embodiment with an initial decoding of a reference on the assay 21. For instance, the optical sensor may decode an assay reference, e.g. any of the reference embodiments previously shown or described, to initially set-up the system in a predetermined format for the particular testing application. For instance, the optical sensor may decode the assay reference to initiate a particular diagnostic test, incubation environment or the like.

Figure 18:
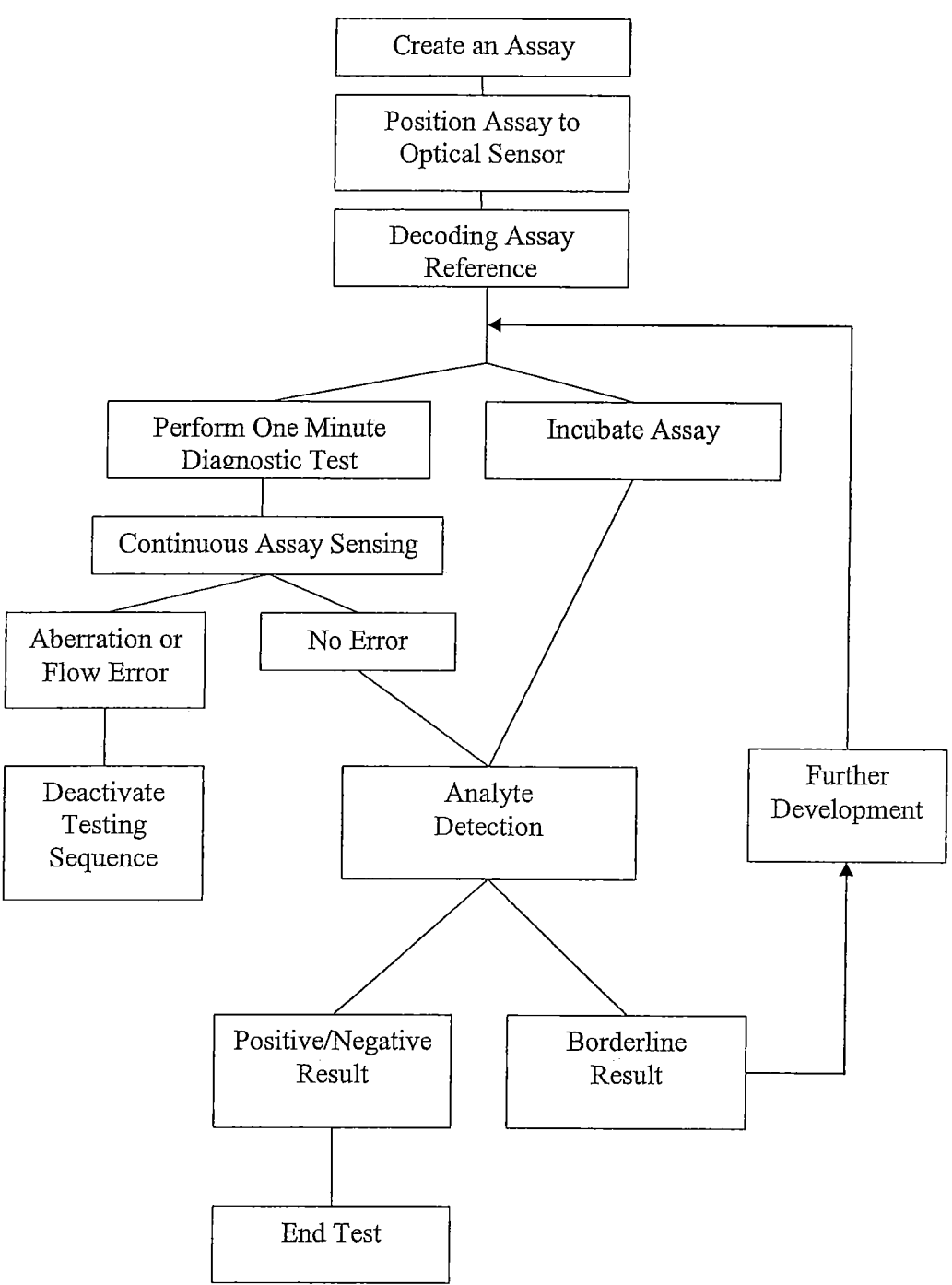
FIG. 18 is yet another flowchart of a diagnostic testing sequence according to one embodiment of the disclosure.

FIG. 18 illustrates yet another testing sequence of the present disclosure. Again, the diagnostic test sequence typically begins with creating an assay 21. For instance, creating the assay 21 may include adding a test sample to a test medium, such as a lateral flow test strip, e.g. including any of the test strip embodiments previously shown or described. Typically, the test medium is configured to provide a detectable test result after incubation with the test sample. Next, the assay 21 is positioned to an optical sensor, e.g. including any of the sensor embodiments previously shown or described. The optical sensor is generally capable of reading reflectance, refractance, and the like from the test medium. The optical sensor may additionally decode an assay reference, e.g. any of the reference embodiments previously shown or described. Further, a preset parameter may be monitored to determine whether adequate flow of reagents occurred on the test strip and whether one or more test lines are present on the test strip prior to being contacted by the test sample.

The assay 21 then undergoes diagnostic testing concurrently with incubation as described herein for the definitive detection of an analyte. As indicated in FIG. 18, the assay 21 may be continuously analyzed during the testing sequence. For instance, the optical sensor may continuously sense reflectance values on the assay 21 as described herein. Any aberration or flow error, e.g. any of the error messages described herein, may deactivate a testing sequence. However, a proper testing sequence, e.g. with no aberrations or flow errors, will proceed to the detection of a presence or absence of an analyte. A definitive test result can be determined by a comparison between changes, such as reflectance changes, in a first line, for example a test line, and a second line, for example a control line, on the test strip. Again, a clear positive or clear negative test result, i.e. a definitive presence or a definitive absence, detection of an analyte will typically end the testing sequence. However, a borderline result will trigger a further development in the testing sequence. Typically, the further development includes continued optical sensing of the assay 21 with concurrent incubation. When a borderline preliminary result is detected, further development is performed until a clear positive or clear negative test result is detected. This definitive presence or definitive absence detection of an analyte typically ends the testing sequence. Those of ordinary skill in the art having the benefit of this disclosure will recognize additional examples of analyzing a borderline test result to generate a definitive test result, i.e. any of the presence or absence test results shown and described herein.

FIGS. 19-23 illustrate particular embodiments of an in-line testing assembly for testing/delivery from supply 302, for instance a milk tank, about a recirculation loop 304 to a downstream delivery 324. As shown, the supply 302 generally includes at least one outlet for access to delivery supply line 308, that may be in fluid communication with the recirculation loop 304. The assembly may include an autosampler 306 to deliver a sample, i.e. any of the samples shown and described herein, to a reader 100, i.e. any of the reader embodiments and examples shown and described herein. The assembly generally includes closures, including valves, cutoffs, alternative delivery systems, and the like. As shown, the assembly includes at least one valve closure 312 for blocking access to delivery output 322. Further shown is at least one valve closure 310 for blocking access to recirculation loop 304. The assembly may additionally include a plurality of supplemental conduits 350, 350'; as well as pumps, for instance to drive flow about the recirculation loop 304.

In one embodiment, an in-line testing and product delivery process includes a supply tank supporting a dairy batch supply adapted for mixing into a homogenous mixture via mechanical devices and/or blades, turbulence, and the like. As shown, supply tank 302 includes an outlet to receive the homogenous mixture in fluid communication with recirculation loop 304 and a downstream delivery output 322. A delivery output valve is aligned between the outlet and delivery output 322. In an open position, delivery output valve releases supply from tank 302 through delivery output 322 to a downstream delivery 324. In a closed position, delivery output valve blocks supply from tank 302 to delivery output 322. As shown and described herein, the various test result readings trigger opening and closing of the delivery output valve. For instance, a positive test result generated by any of the reader embodiments herein enables closure of delivery output valve, i.e. blocking access to downstream delivery 324. While a negative test result generated by any of the reader embodiments herein opens delivery output valve to release supply through delivery output 322, and in certain examples to downstream delivery 324.

In certain embodiments, a recirculation loop valve is aligned between the tank outlet and recirculation loop 304. In an open position, recirculation loop valve allows supply from tank 302 to enter the recirculation loop 304. A pump, gravity fed system, or the like may maintain constant pressure of supply within recirculation loop 304 when recirculation loop valve is open. As shown and described herein, recirculation loop 304 may thereby be a closed loop system in fluid communication with the tank outlet and the supply in tank 302. In a closed position, recirculation loop valve blocks supply from tank 302 into the recirculation loop 304. In particular embodiments, a user interface activates the recirculation loop valve to bypass the recirculation loop 304, autosamplers, and/or any of the readers shown and described herein, for instance for isolated testing of supply using any of the readers and assay analysis shown and described herein.

A sample valve may be positioned in the recirculation loop 304 to release a supply sample from the recirculation loop 304 to a testing sequence. In particular examples, sample valve may be an autosampler and the like. For instance, autosampler 306 may deliver a predetermined volume of sample, i.e. any of the samples shown and described herein, to a reader 100, 300, 400, i.e. any of the reader embodiments and examples shown and described herein. Flow from the recirculation loop 304, for instance through autosampler 306, may be triggered by closure of hood 402, 502, activated by a user, or otherwise automated. The autosampler 306 may deliver 320 any volume of sample, including, but not limited to, about 0.3 mL to any of the assays shown and described herein. In one example, autosampler 306 may deliver 320 sample through entry portal 454 protruding through hood 402, 502, to the reader for rapidly detecting a presence or absence of an analyte. As illustrated in FIG. 19a, opposing entry portal 454 may be a puncture tip 452 protruding from hood 402, 502 to puncture any of the assays shown and described herein to expedite delivery of sample into the assay for rapid testing. In particular examples, a syringe tip, for instance via a leer lock syringe, delivers sample into the assay, however those skilled in the art having the benefit of this disclosure will recognize additional other tip and syringe alternatives. As further shown in FIG. 19, in one closed flow example an air line 320' may run parallel sample delivery line 320 into air entry 464 of hood 402, 502 and exit 450 as shown and described herein. In addition, in certain examples the processes and assemblies herein reduce, or even eliminate, cross-contamination by in-line cleaning along the sample and product flow path, including in-line cleaning of any of the elements and components shown and described herein. Further, in certain examples any of the elements and components herein may be disposable, removable from the flow path, and the like to minimize, or eliminate cross-contamination.

Figure 20:
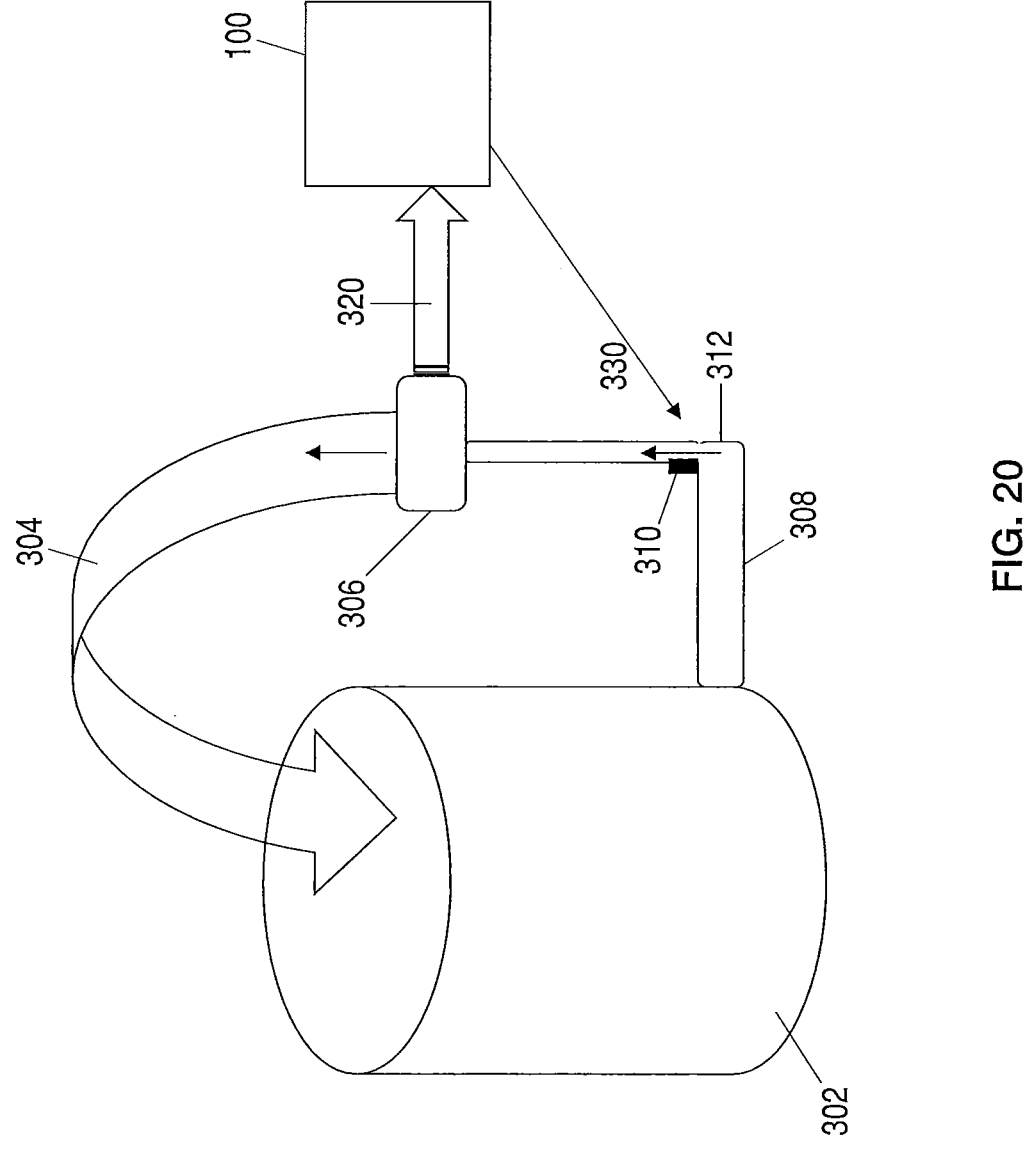
FIG. 20 is a partial schematic of a positive-result system flow embodiment introduced in FIG. 19, with elements removed for clarity.
Figure 21:
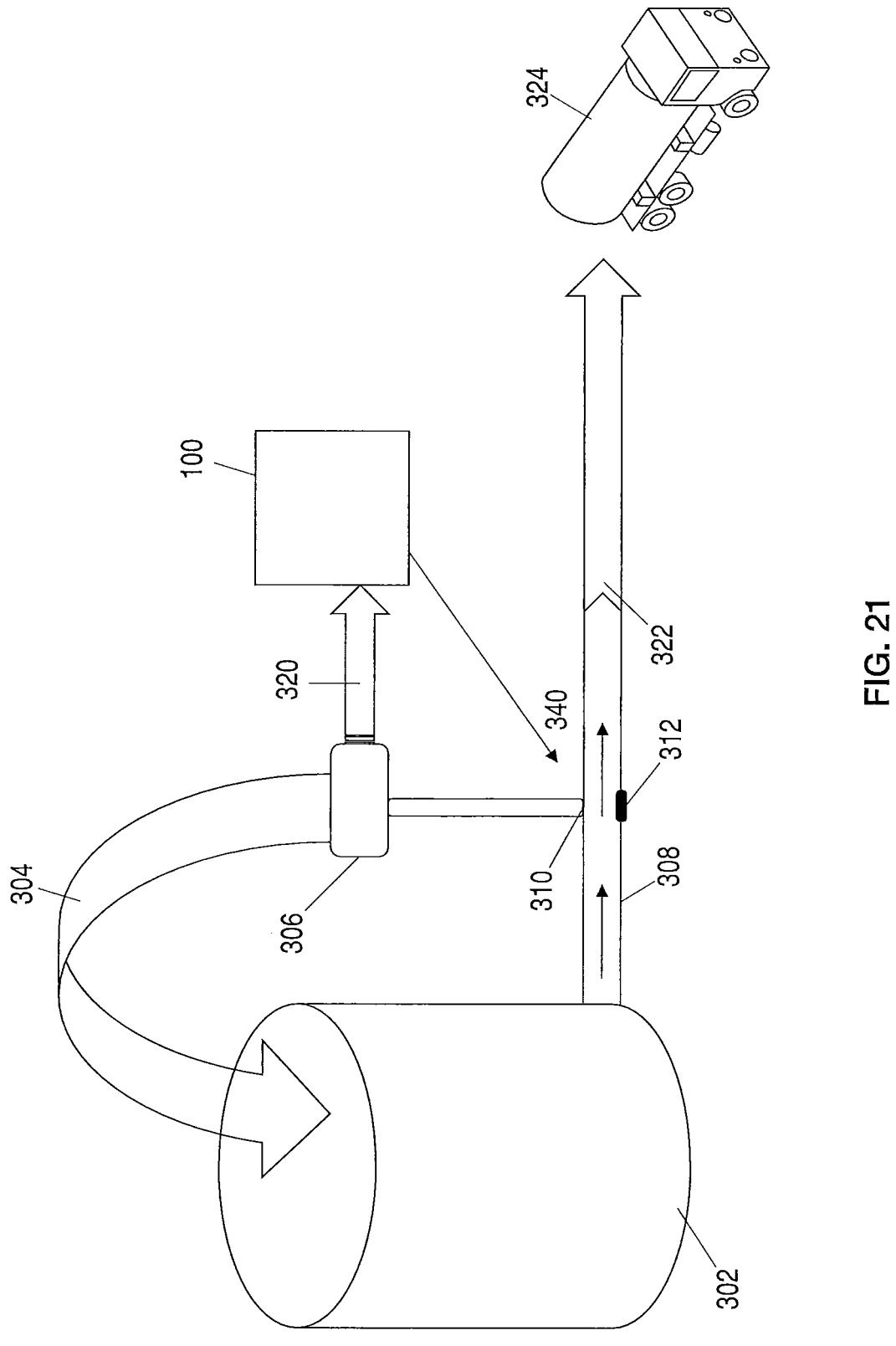
FIG. 21 is a partial schematic of a negative-result system flow embodiment introduced in FIG. 19, with elements removed for clarity.

FIG. 20 illustrates one embodiment of a positive test result loop activated by a positive test result reading 330, i.e. any of the positive test result examples and embodiments shown and described herein. FIG. 21 illustrates one embodiment of a negative test result loop activated by a negative test result reading 340, i.e. any of the negative test result examples and embodiments shown and described herein.

Figure 23:
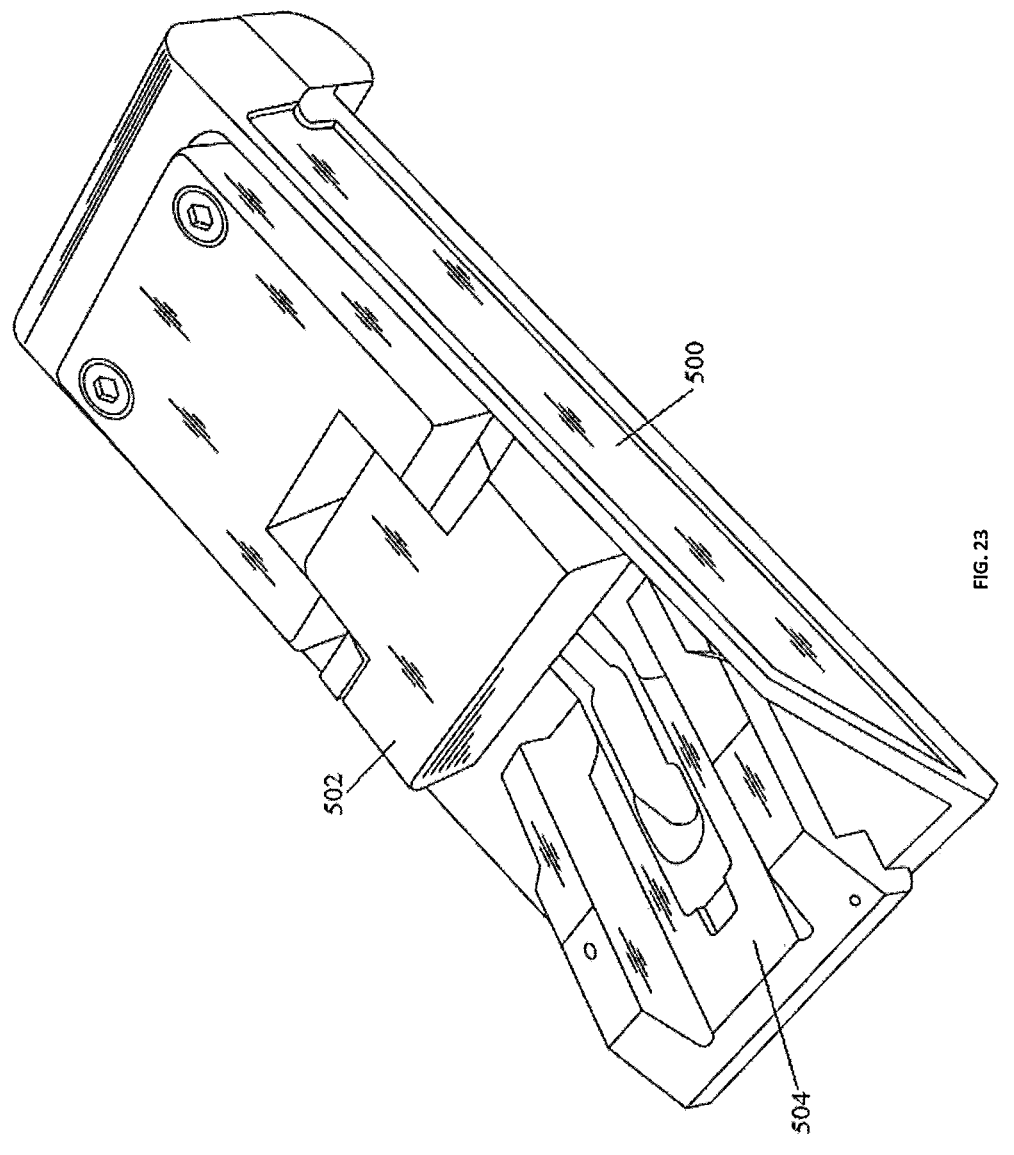
FIG. 23 is a side perspective view of an isolated alternative inclined cavity, with elements removed for clarity.

As shown in FIG. 23, one embodiment of lateral flow assay system 500 includes an elongated channel configured to receive and maintain an assay in an inclined position to minimize impact of sample drippage, and the like, from in-line sample testing along the assay while generating any of the diagnostic test result shown and described herein. As illustrated, lateral flow assay system 500 includes an inclined cavity 504 having a proximate portion to receive a capillary-flow test strip and an opposing distal portion aligned above the proximate portion. In certain examples, the inclined cavity 504 may be aligned between about twenty degrees to about sixty degrees, including, but not limited to, about forty-five degrees from the horizontal to position and maintain the assay in an optical alignment with the reader. As shown, light can be directed to the assay, for example through an aperture in the inclined cavity 503, and then reflected off the assay, back through the inclined cavity aperture and directed to an optical detector.

In certain embodiments, software applications, instrumentation, systems, and assemblies may provide real time data collection of test data, including but not limited to field data, using data communication exchange, including Bluetooth® Interface and the like, adapters and widely utilized phone, and similar personal device, technologies. For instance, one instrument relay embodiment may include generating a test result on any of the testing instrument readers shown and described herein; communicating the test result to a partner device module; and relaying a test result output to an external host module. Further, any of the testing instrument readers herein may interface directly with the external storage configuration. In particular examples, the partner device is a smart phone, however other partner devices may include a tablet, a general purpose computer, a PDA, a digital media player, a digital camera, a wireless information device, and the like.

The partner device may connect to the external storage configuration in a variety of modes. In a remote access mode, the partner device links to an available testing instrument and allows the system to deliver test data to the external storage configuration. The partner device may have an indicator, and when activated providing a pairing signal, and wherein the indicator providing a visual indicia of pairing to the testing instrument reader.

In particular embodiments, a partner device is in a local data communication, such as wireless Bluetooth® transmission/receipt, with a testing instrument. Further, the partner device is in host exchange communication, including any mobile telecommunications communication technology such as Wi-Fi, 3G/4G/5G connectivity, with an external host. In certain modules, the testing instrument interfaces with a mobile partner device having a corresponding data communication interface, thereby establishing enabled, i.e. approved, authorized, and/or available, data communication with the testing instrument. In particular examples, the module may include linking an application, for instance a downloadable program application, on the partner device to the testing instrument. Further, the module may include establishing data communication exchange of a result output between the testing instrument and the partner device. Still further, the module may include establishing a secondary messaging data communication, including but not limited to email, text, and the like, secondary message exchange between the testing instrument and the partner device.

Typically, the partner device relays result outputs to an external storage configuration. In particular examples, relaying to the external storage configuration includes transmitting to a remote host website. In other examples, relaying to the external storage includes transmitting to a remote host server. In yet other examples, relaying to the external storage includes transmitting to two or more host providers for data storage and management.

In certain embodiments, the testing instrument interfaces with a mobile partner device having a corresponding data communication interface, thereby establishing enabled, i.e. approved, authorized, and/or available, data communication with the testing instrument. In particular examples, the module may include linking an application, for instance a downloadable program application, on the partner device to the testing instrument. Further, the module may include establishing data communication exchange of a result output between the testing instrument and the partner device. Still further, the module includes establishing a secondary messaging data communication, including but not limited to email, text, and the like, secondary message exchange between the testing instrument and the partner device. The partner device may relay result outputs to an external storage configuration. In particular examples, relaying to the external storage configuration includes transmitting to a remote host website. In other examples, relaying to the external storage includes transmitting to a remote host server. In yet other examples, relaying to the external storage includes transmitting to two or more host providers for data storage and management.

Particular methods for analyte analysis includes incubating the assay, e.g. including any of the embodiments previously shown or described, and reading the assay to generate a test result, e.g. including any of the embodiments previously shown or described. In particular examples, a diagnostic test method for detecting an analyte in a test sample includes adding a test sample to a test medium, such as a lateral flow test strip, to create an assay, the test medium configured to provide a detectable test result after incubation with the test sample; enclosing the test medium within a hood, the hood configured to enclose a cavity, the cavity configured to receive the test medium and connected with a temperature control source, the temperature control source capable of maintaining a consistent temperature; positioning a sensor, such as an optical sensor capable of reading reflectance from the test medium, relative to the test medium so that a change on the test medium is detectable by the sensor; and activating the sensor, such as by closing the hood, the activation causing the sensor to compare the test medium to a preset parameter. When the test medium is not within the preset parameter, a test result is not provided, and wherein when the test medium is within the preset parameter, the test result is determined from the test medium, the test result indicating whether an analyte was detected in the test sample.

In other embodiments of the methods, a preset parameter can be used to determine either or both whether an adequate flow of reagents occurred on the test strip while the test strip was within the cavity and whether one or more test lines are present on the test strip prior to being contacted by the test sample. To do so the sensor can be configured to continuously analyze changes on the test medium until a test result occurs. The test result can be determined by a comparison between changes, such as reflectance changes, in a first line, for example a test line, and a second line, for example a control line, on the test strip.

A further example of the methods include using preset parameters to compare the test strip, prior to sample flow thereon, including prior to sample application, with the actual strip being used. For example, a blank strip, prior to reagent flow or prior to sample application, will have a theoretical reflectance profile within a predictable range. If areas of reduced reflectance are detected, that did not result from sample/reagent flow on the strip, then it is possible not only that something untoward has occurred with the test strip but also it is possible that the optical path has become contaminated and requires cleaning. Such contamination can be on the strip or within the reader. Generally, an unused test strip should have no areas of reduced reflectance. Any such areas can indicate a problem, whether from dirt/debris, use of a test strip that was already run, or otherwise. In any case, the test result may not be valid.

Numerous characteristics and advantages have been set forth in the foregoing description, together with details of structure and function. Many of the novel features are pointed out in the appended claims. The disclosure, however, is illustrative only, and changes may be made in detail, especially in matters of shape, size, and arrangement of parts, within the principle of the disclosure, to the full extent indicated by the broad general meaning of the terms in which the general claims are expressed. It is further noted that, as used in this application, the singular forms "a," "an," and "the" include plural referents unless expressly and unequivocally limited to one referent.

We claim:

1. An in-line testing and product delivery assembly, said assembly comprising:

a. a supply of product having at least one outlet;

b. a sample feed in fluid communication with said supply of product to divert a portion of said product for testing;

c. a reader to receive a sample from said sample feed and generate a test result from an assay for detecting a presence or absence of an analyte, said reader having a defined inclined imaging cavity with a proximate cavity portion and a distal cavity portion, wherein said proximate cavity portion aligns a first end of said assay vertically offset below said distal cavity portion to incline a second end of said assay in a predetermined inclined imaging position having an incline angle from horizontal and an optical detector positioned to image said assay positioned within said inclined imaging cavity and an incubator providing a controlled incubation temperature during imaging; and d. a delivery line in fluid communication with said at least one outlet and having a delivery output valve, and detection of said analyte triggers a closure of said delivery output valve, and a detection of an absence of said analyte triggers an opening of said delivery output valve to release said supply of product through said delivery line.

2. The assembly of claim 1, wherein said reader includes a hood to removably receive said assay, and wherein said hood comprises a puncture tip protruding to puncture said assay.

3. The assembly of claim 2, wherein said hood includes a sample supply line in fluid communication with said sample feed to dispense sample into said assay.

4. The assembly of claim 3, wherein said sample feed aligned adjacent said puncture tip to dispense sample into said assay at said puncture tip.

5. The assembly of claim 1, wherein said inclined cavity having an elongated channel receiving and maintaining said assay in an inclined testing position.

6. The assembly of claim 5, wherein said inclined cavity having a proximate portion and an opposing distal portion, wherein said distal portion positioned above said proximate portion at about a forty-five degree incline.

7. The assembly of claim 1, wherein said reader generates a definitive test result within about fifteen seconds to about one minute.

8. The assembly of claim 7, wherein said reader generates a definitive test result within about thirty seconds.

9. The assembly of claim 1, including an auto-sampler in fluid communication with said sample feed.

10. The assembly of claim 1, wherein said sample feed being a closed loop recirculation system about said supply of product.

11. The assembly of claim 10, including an auto-sampler in fluid communication with said closed loop system at a sample release valve, wherein said recirculation loop being in fluid communication with said at least one outlet and having a re-entry fluid communication with said supply of product.

12. The assembly of claim 10, wherein at least a portion of said recirculation loop being a single use disposable conduit.

13. The assembly of claim 10, wherein said recirculation loop includes a pump.

14. The assembly of claim 1, wherein said assay comprises a single-use test strip.

15. The assembly of claim 1, wherein said reader's optical detector detects a first transmission of light on said assay and detects at least a subsequent transmission of light on said assay, and wherein incubation of said assay and detection of said transmissions of light on said assay generates said test result.

16. The assembly of claim 1, wherein said reader generates at least one borderline test result.

* * * * *